US012077830B2

(12) United States Patent
Lee et al.

(10) Patent No.: US 12,077,830 B2
(45) Date of Patent: Sep. 3, 2024

(54) METHODS FOR DETECTING NOROVIRUS

(71) Applicant: Quest Diagnostics Investments LLC, Secaucus, NJ (US)

(72) Inventors: Peter Lee, Tustin, CA (US); Raymond Huang, Cerritos, CA (US); Kristin Ramos, Carson, CA (US); Jules Chen, Irvine, CA (US); Michelle Tabb, Santa Ana, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 42 days.

(21) Appl. No.: 18/097,004

(22) Filed: Jan. 13, 2023

(65) Prior Publication Data

US 2023/0279513 A1 Sep. 7, 2023

Related U.S. Application Data

(60) Division of application No. 17/063,078, filed on Oct. 5, 2020, now Pat. No. 11,555,223, which is a continuation of application No. 16/306,203, filed as application No. PCT/US2017/035686 on Jun. 2, 2017, now Pat. No. 10,793,924.

(60) Provisional application No. 62/345,331, filed on Jun. 3, 2016.

(51) Int. Cl.
*C12Q 1/70* (2006.01)
*A61P 31/14* (2006.01)
*C12N 7/00* (2006.01)
*C12Q 1/68* (2018.01)
*C12Q 1/686* (2018.01)
*G01N 33/569* (2006.01)
*A61K 39/00* (2006.01)

(52) U.S. Cl.
CPC .............. *C12Q 1/701* (2013.01); *A61P 31/14* (2018.01); *C12N 7/00* (2013.01); *C12Q 1/68* (2013.01); *C12Q 1/686* (2013.01); *C12Q 1/70* (2013.01); *G01N 33/56983* (2013.01); *A61K 39/00* (2013.01); *C12N 2770/16021* (2013.01); *C12Q 2600/106* (2013.01); *C12Q 2600/112* (2013.01); *G01N 2333/08* (2013.01)

(58) Field of Classification Search
CPC ......... A61K 39/00; A61K 39/12; A61P 31/14; C12N 2770/16021; C12N 7/00
See application file for complete search history.

(56) References Cited

U.S. PATENT DOCUMENTS

| | | | |
|---|---|---|---|
| 5,677,124 A | 10/1997 | Dubois et al. |
| 7,202,032 B2 | 4/2007 | Kageyama et al. |
| 2003/0180894 A1 | 9/2003 | Masuda et al. |
| 2006/0110724 A1 | 5/2006 | Burkhardt et al. |
| 2011/0195113 A1 | 8/2011 | Richardson et al. |
| 2013/0022963 A1 | 1/2013 | Exner et al. |

FOREIGN PATENT DOCUMENTS

| | | |
|---|---|---|
| CN | 105177185 A | 12/2015 |
| WO | WO-2016/085955 A1 | 6/2016 |

OTHER PUBLICATIONS

Office Action dated Dec. 8, 2023 in EP 17807569.3.
Beuret, Christian, "Simultaneous detection of enteric viruses by multiplex real-time RT-PCR," Journal of Virological Methods, Jan. 1, 2004, 115(1):1-8.
Hall et al., "Evaluation of Inhibitor-Resistant Real-Time PCR Methods for Diagnostics in Clinical and Environmental Samples," PLoS One, Sep. 9, 2013, 8(9):e73845, 1-8.
International Search Report dated Sep. 18, 2017, in PCT/US2017/035686.
Naylor et al., "Identification of Canine Coronavirus Strains from Feces by S Gene Nested PCR and Molecular Characterization of a New Australian Isolate," Journal of Clinical Microbiology, Mar. 2001, 39(3):1036-1041.
Nishimura et al., "Detection of noroviruses in fecal specimens by direct RT-PCR without RNA purification," Journal of Virological Methods, Feb. 1, 2010, 163(2):282-286.
Radin et al., "Evaluation of Two Primer Sets Using Newly Developed Internal Amplification Controls for Rapid Human Norovirus Detection by SYBR Green I Based Real-Time RT-PCT," Food Environ. Virol., Jun. 1, 2011, 3(2):61-69.
Supplementary European Search Report in EP 17807569.3 dated Dec. 3, 2019.
Yan et al., "A one-step multiplex real-time RT-PCR assay for rapid and simultaneous detection of human norovirus genogroup I, II and IV," Journal of Virological Methods, May 1, 2013, 189(2):277-282.

*Primary Examiner* — Barry A Chestnut
(74) *Attorney, Agent, or Firm* — Foley & Lardner LLP

(57) ABSTRACT

The present disclosure provides methods and compositions for determining whether a patient exhibiting acute gastroenteritis will benefit from treatment with therapeutic agents that inhibit Norovirus genogroup I (GI) or Norovirus genogroup II (GII). The methods disclosed herein are based on detecting Norovirus genogroup I (GI) and Norovirus genogroup II (GII) in a stool sample without extracting viral nucleic acids from a clinical specimen prior to performing real-time reverse transcription PCR. Kits for use in practicing the methods are also provided.

13 Claims, No Drawings

Specification includes a Sequence Listing.

METHODS FOR DETECTING NOROVIRUS

CROSS REFERENCE TO RELATED APPLICATION

This application is a Divisional of U.S. application Ser. No. 17/063,078, filed Oct. 5, 2020, which is a Continuation of U.S. application Ser. No. 16/306,203, which is the U.S. National Stage of PCT/US2017/035686, filed Jun. 2, 2017, which claims the benefit of and priority to U.S. Application No. 62/345,331 filed Jun. 3, 2016, the contents of which are incorporated herein by reference in their entireties.

SEQUENCE LISTING

The instant application contains a Sequence Listing which has been submitted electronically in XML format and is hereby incorporated by reference in its entirety. Said XML copy, created on Mar. 22, 2023, is named 034827-1912_SL.xml and is 34,376 bytes in size.

TECHNICAL FIELD

The present disclosure provides methods and compositions for determining whether a patient suffering from acute gastroenteritis will benefit from treatment with therapeutic agents that inhibit Norovirus genogroup I (GI) or Norovirus genogroup II (GII). The methods of the present technology are based on detecting Norovirus genogroup I (GI) and Norovirus genogroup II (GII) in a stool sample without extracting viral nucleic acids from a clinical specimen prior to performing real-time reverse transcription PCR (RT-PCR). Kits for use in practicing the methods are also provided.

BACKGROUND

The following description of the background of the present disclosure is provided simply to aid the reader in understanding the disclosure and is not admitted to describe or constitute prior art to the present disclosure.

Norovirus is a non-enveloped, single-stranded RNA virus in the Caliciviridae family and is responsible for 60% to 80% of all human gastroenteritis outbreaks worldwide. Human Noroviruses are responsible for approximately 21-23 million gastroenteritis cases and 800 deaths in the USA and over 218,000 deaths in developing nations annually, mostly in children less of 5 years of age.

Human Noroviruses have an incubation period of approximately 24 hrs and a disease length of approximately 24-72 hrs. The most common symptoms are nausea, vomiting and diarrhea, but can also include abdominal cramps, fever, headache and dehydration. Noroviruses are primarily transmitted via the fecal-oral route, but can also be transmitted via aerosolized vomitus droplets, contaminated food or water and fomites. Human Noroviruses are highly contagious and can cause large outbreaks in a wide variety of settings, including healthcare facilities, cruise ships, restaurants and schools.

Rapid and accurate detection of Norovirus infections is important in preventing the spread of the virus in healthcare and non-healthcare settings. Noroviruses are divided into six genogroups (GI-GVI). GII genotype 4 (GII.4) Noroviruses account for approximately 60-90% of all human Noroviruses gastroenteritis annually. The GI and GII genogroups are the most prevalent in terms of human infection, but are believed to lack common neutralization epitopes due to major antigenic differences between them. The tremendous viral diversity makes the development of broadly protective human Norovirus vaccines very challenging.

Thus, there is a substantial need for more robust and sensitive methods that can rapidly detect and discriminate between multiple Norovirus genogroups, such as Norovirus genogroup I (GI) or Norovirus genogroup II (GII) in clinical stool samples.

SUMMARY

The present disclosure provides compositions and methods for detecting and discriminating between multiple Norovirus genogroups, such as Norovirus genogroup I (GI) or Norovirus genogroup II (GII) in a composite biological sample such as stool. The methods of the present technology may be practiced on unprocessed stool samples, resulting in a direct, streamlined sample-to-result process. In another aspect, the methods and compositions of the present technology are useful in selecting an optimal therapeutic regimen for a subject suffering from acute gastroenteritis. It is contemplated that the methods disclosed herein allow for rapid, sensitive and simultaneous detection of one or more target nucleic acid sequences corresponding to Norovirus genogroup I (GI) or Norovirus genogroup II (GII).

Accordingly, in one aspect, the present disclosure provides a method for detecting the presence of at least one Norovirus genogroup in a stool sample comprising: contacting the stool sample with: (i) a first primer pair that amplifies a Norovirus genogroup I (GI) target nucleic acid comprising nucleotides that are at least 80-95% identical to SEQ ID NO: 2 or a complement thereof, and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample. In some embodiments, the method further comprises (a) subjecting the reaction-sample mixture to real-time reverse transcription polymerase chain reaction ("RT-PCR") conditions under which each of the target nucleic acids present in the stool sample is amplified to produce a fluorescent signal; (b) detecting the fluorescent signal generated by each amplified target nucleic acid produced in step (a); and (c) detecting the presence of at least one Norovirus genogroup in the stool sample by evaluating the fluorescent signal of each target nucleic acid, wherein detection of the Norovirus genogroup I (GI) target nucleic acid is indicative of the presence of Norovirus genogroup I (GI) in the stool sample; and detection of the Norovirus genogroup II (GII) target nucleic acid is indicative of the presence of Norovirus genogroup II (GII) in the stool sample; and wherein the stool sample is not subjected to an extraction or purification step prior to amplification. Real-time RT-PCR amplification may be performed in a direct amplification disc in concert with an integrated thermal cycler. In some embodiments, Norovirus genogroup I (GI) comprises one or more genotypes selected from the group consisting of GI.1, GI.2, GI.3, GI.4, GI.5, GI.6, GI.7, GI.8, GI.9, GII.10 and GI.14. In certain embodiments, Norovirus genogroup II (GII) comprises one or more genotypes selected from the group consisting of GII.1, GII.2, GII.3, GII.4, GII.5, GII.6, GII.7, GII.8, GII.9, GII.10, GII.11, GII.12, GII.13, GII.14, GII.15, GII.16, GII.17, GII.18, GII.19, GII.20, GII.21, GII.22, and GII.23. In some embodiments, the stool sample comprises unformed stool, formed stool, or a rectal swab stored in liquid Amies media.

All primer pairs may be contained together in an amplification master mix further comprising DNA polymerase, dNTPs and PCR buffer prior to contacting the stool sample. In addition, the amplification master mix may further comprise a third primer pair that specifically hybridizes under stringent conditions to a control target nucleic acid.

The stool sample may be brought into contact with one or more of the primer pairs separately or simultaneously. Where the contact occurs simultaneously (i.e. multiplexing), one or both of the first and second primer pairs are brought into contact with the stool sample and with each other to amplify the target nucleic acid sequences.

In some embodiments of the method, the first primer pair consists of a first forward primer comprising 5'd CGYTGGATGCGITTYCATGA 3'(SEQ ID NO: 5) and a first reverse primer comprising 5'd TCCTTAGACGCCATCATCATTTAC 3' (SEQ ID NO: 6). Additionally or alternatively, in some embodiments, the second primer pair consists of a second forward primer comprising 5'd TGTTYAGGTGGATGAGRTTCTCIGA 3' (SEQ ID NO: 9) and a second reverse primer comprising 5'd TCGACGCCATCTTCATTCACA 3' (SEQ ID NO: 10).

Optionally, a control target nucleic acid and a third primer pair complementary to the control target nucleic acid may be included in the amplification mixture. In some embodiments, the control target nucleic acid comprises SEQ ID NO: 12 or a complement thereof. In certain embodiments, the third primer pair consists of a third forward primer comprising 5'd CTCGTCGACAATGGCGGAA 3' (SEQ ID NO: 13) and a third reverse primer comprising 5'd TTCAGCGACCCCGTTAGC 3' (SEQ ID NO: 14).

In some embodiments, the method further comprises contacting the stool sample with a first nucleic acid probe that is capable of specifically hybridizing to a segment of the Norovirus genogroup I (GI) target nucleic acid sequence of SEQ ID NO: 2 or a complement thereof, wherein the first nucleic acid probe is detectably labeled and comprises 5'd TGGACAGGAGAYCGCIATCTCYTGCCCGA 3' (SEQ ID NO: 7) or a complement thereof. Additionally or alternatively, in some embodiments, the method further comprises contacting the stool sample with a second nucleic acid probe that is capable of specifically hybridizing to a segment of the Norovirus genogroup I (GI) target nucleic acid sequence of SEQ ID NO: 2 or a complement thereof, wherein the second nucleic acid probe is detectably labeled and comprises 5'd TGGACAGGAGATCGCAATCTACTGCCTGA 3'(SEQ ID NO: 8) or a complement thereof.

Additionally or alternatively, in some embodiments, the method further comprises contacting the stool sample with a third nucleic acid probe that is capable of specifically hybridizing to a segment of the Norovirus genogroup II (GII) target nucleic acid sequence of SEQ ID NO: 4 or a complement thereof, wherein the third nucleic acid probe is detectably labeled and comprises 5'd ACGTGGGAGGGCGATCGCAATCT 3' (SEQ ID NO: 11) or a complement thereof.

In certain embodiments of the method, the first nucleic acid probe is detectably labelled with CFR610 fluorophore, the second nucleic acid probe is detectably labelled with CFR610 fluorophore, and the third nucleic acid probe is detectably labelled with FAM fluorophore.

In any of the above embodiments, the method further comprises contacting the stool sample with a fourth nucleic acid probe that specifically hybridizes to a segment of the control target nucleic acid or a complement thereof, wherein the fourth nucleic acid probe is detectably labeled and comprises 5'd GCTTGGGGCGACAGTCACGTCGC 3' (SEQ ID NO: 15) or a complement thereof. In some embodiments, the fourth nucleic acid probe is detectably labelled with Q670 fluorophore.

In another aspect, the present disclosure provides a method for selecting a patient suffering from acute gastroenteritis for treatment with a therapeutic agent that inhibits Norovirus genogroup II (GII) comprising: contacting a stool sample obtained from the patient with: (i) a first primer pair that amplifies a Norovirus genogroup I (GI) target nucleic acid comprising nucleotides that are at least 80-95% identical to SEQ ID NO: 2 or a complement thereof; and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample. In some embodiments, the method further comprises (a) subjecting the reaction-sample mixture to real-time RT-PCR conditions under which each of the target nucleic acids present in the stool sample is amplified to produce a fluorescent signal; (b) detecting the fluorescent signal generated by each amplified target nucleic acid produced in step (a); and (c) selecting the patient for treatment with a therapeutic agent that inhibits Norovirus genogroup II (GII), if a fluorescent signal for the Norovirus genogroup II (GII) target nucleic acid is detected, wherein the stool sample is not subjected to an extraction or purification step prior to amplification. In some embodiments, real-time RT-PCR amplification is performed in a direct amplification disc in concert with an integrated thermal cycler.

In some embodiments of the method, the first primer pair consists of a first forward primer comprising 5'd CGYTGGATGCGITTYCATGA 3'(SEQ ID NO: 5) and a first reverse primer comprising 5'd TCCTTAGACGCCATCATCATTTAC 3' (SEQ ID NO: 6). Additionally or alternatively, in some embodiments, the second primer pair consists of a second forward primer comprising 5'd TGTTYAGGTGGATGAGRTTCTCIGA 3' (SEQ ID NO: 9) and a second reverse primer comprising 5'd TCGACGCCATCTTCATTCACA 3' (SEQ ID NO: 10).

Optionally, a control target nucleic acid and a third primer pair complementary to the control target nucleic acid may be included in the amplification mixture. In some embodiments, the control target nucleic acid comprises SEQ ID NO: 12 or a complement thereof. In certain embodiments, the third primer pair consists of a third forward primer comprising 5'd CTCGTCGACAATGGCGGAA 3' (SEQ ID NO: 13) and a third reverse primer comprising 5'd TTCAGCGACCCCGTTAGC 3' (SEQ ID NO: 14).

In some embodiments, the method further comprises contacting the stool sample with a first nucleic acid probe that is capable of specifically hybridizing to a segment of the Norovirus genogroup I (GI) target nucleic acid sequence of SEQ ID NO: 2 or a complement thereof, wherein the first nucleic acid probe is detectably labeled and comprises 5'd TGGACAGGAGAYCGCIATCTCYTGCCCGA 3' (SEQ ID NO: 7) or a complement thereof. Additionally or alternatively, in some embodiments, the method further comprises contacting the stool sample with a second nucleic acid probe that is capable of specifically hybridizing to a segment of the Norovirus genogroup I (GI) target nucleic acid sequence of SEQ ID NO: 2 or a complement thereof, wherein the second nucleic acid probe is detectably labeled and comprises 5'd TGGACAGGAGATCGCAATCTACTGCCTGA 3'(SEQ ID NO: 8) or a complement thereof. Additionally or alternatively, in some embodiments, the method further comprises contacting the stool sample with a third nucleic acid probe that is capable of specifically hybridizing to a segment of the Norovirus genogroup II (GII) target nucleic acid sequence of SEQ ID NO: 4 or a complement thereof, wherein the third nucleic acid probe is detectably labeled and comprises 5'd ACGTGGGAGGGCGATCGCAATCT 3' (SEQ ID NO: 11) or a complement thereof.

In certain embodiments of the method, the first nucleic acid probe is detectably labelled with CFR610 fluorophore, the second nucleic acid probe is detectably labelled with CFR610 fluorophore, and the third nucleic acid probe is detectably labelled with FAM fluorophore.

In any of the above embodiments, the method further comprises contacting the stool sample with a fourth nucleic acid probe that specifically hybridizes to a segment of the control target nucleic acid or a complement thereof, wherein the fourth nucleic acid probe is detectably labeled and comprises 5'd GCTTGGGGCGACAGTCACGTCGC 3' (SEQ ID NO: 15) or a complement thereof. In some embodiments, the fourth nucleic acid probe is detectably labelled with Q670 fluorophore.

In some embodiments, the therapeutic agent that inhibits Norovirus genogroup II (GII) is one or more agents selected from the group consisting of GII.4/VA387-derived P particle vaccines (Kocher J et al., *J Virol.* 88(17):9728-9743 (2014)), GII.4-derived virus-like particles (VLPs) vaccines (Souza M et al., *Vaccine* 25(50):8448-8459 (2007); Debbink K et al., *J Virol.* 88(13):7256-7266 (2014)), VLPs derived from a consensus GII.4 sequence and Norwalk virus with Alhydrogel adjuvant (Parra G I et al., *Vaccine* 30(24):3580-3586 (2012)), and VLPs derived from GII.4 Human Norovirus VP1 with rotavirus VP6 antigen (Blazevic V et al., *Vaccine* 29(45):8126-8133 (2011)).

In one aspect, the present disclosure provides a method for selecting a patient suffering from acute gastroenteritis for treatment with a therapeutic agent that inhibits Norovirus genogroup II (GII) and an additional therapeutic agent that inhibits Norovirus genogroup I (GI) comprising: contacting a stool sample obtained from the patient with: (i) a first primer pair that amplifies a Norovirus genogroup I (GI) target nucleic acid comprising nucleotides that are at least 80-95% identical to SEQ ID NO: 2 or a complement thereof; and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample. In some embodiments, the method further comprises (a) subjecting the reaction-sample mixture to real-time RT-PCR conditions under which each of the target nucleic acids present in the stool sample is amplified to produce a fluorescent signal; (b) detecting the fluorescent signal generated by each amplified target nucleic acid produced in step (a); and (c) selecting the patient for treatment with a therapeutic agent that inhibits Norovirus genogroup II (GII) and an additional therapeutic agent that inhibits Norovirus genogroup I (GI), if (i) a fluorescent signal for the Norovirus genogroup I (GI) target nucleic acid and (ii) a fluorescent signal for the Norovirus genogroup II (GII) target nucleic acid are detected, wherein the stool sample is not subjected to an extraction or purification step prior to amplification.

In some embodiments of the method, the therapeutic agent that inhibits Norovirus genogroup II (GII) is one or more agents selected from the group consisting of GII.4/VA387-derived P particle vaccines (Kocher J et al., *J Virol.* 88(17):9728-9743 (2014)), GII.4-derived virus-like particles (VLPs) vaccines (Souza M et al., *Vaccine* 25(50):8448-8459 (2007); Debbink K et al., *J Virol.* 88(13):7256-7266 (2014)), VLPs derived from a consensus GII.4 sequence and Norwalk virus with Alhydrogel adjuvant (Parra G I et al., *Vaccine* 30(24):3580-3586 (2012)), and VLPs derived from GII.4 Human Norovirus VP1 with rotavirus VP6 antigen (Blazevic V et al., *Vaccine* 29(45):8126-8133 (2011)).

In some embodiments of the method, the additional therapeutic agent that inhibits Norovirus genogroup I (GI) is one or more agents selected from the group consisting of serum histo-blood group antigen (HBGA) blocking antibodies, ribavirin, favipiravir, 2'-C-methylcytidine, suramin-related compounds, IFNs α, β or γ, dipeptidyl inhibitors of norovirus 3CL protease (Kankanamalage et al., *J Med Chem.* 58(7):3144-3155 (2015); Takahashi et al., *Virus Res.* 178(2):437-444 (2013)), Pyridoxal-5'-phosphate-6-(2'-naphthylazo-6'-nitro-4',8'-disulfonate) tetrasodium salt (PPNDS), naphthalene-sulfonate inhibitors of human norovirus RNA-dependent RNA-polymerase (Tarantino et al., *Antiviral Res.* 2014; 102:23-28), naphthalene di-sulfonate (NAF2), non-nucleoside inhibitors, GI.1 plus GII.4 consensus VLP bivalent vaccine (Treanor J J et al., *J Infect Dis.* 210(11):1763-1771 (2014)), and small molecule deubiquitinase inhibitors (Gonzalez-Hernandez M J et al., *PLoS ONE* 9(4):e94491 (2014)).

In another aspect, the present disclosure provides kits comprising oligonucleotides which may be primers or probes for performing amplifications as described herein.

DETAILED DESCRIPTION

Human Noroviruses are a leading cause of acute, non-bacterial gastroenteritis worldwide. Stool is an excellent sample source for diagnosing cases of viral and bacterial gastroenteritis (Tenover et al., *J Mol Diagn.* 13(6): 573-582 (2011); Liu et al., *J Clin Virol.* 50: 308-315 (2011)). However, the isolation of high quality nucleic acids from stool is difficult. The presence of phenolic compounds, metabolites and polysaccharides in stool make the isolation of quality nucleic acid samples that are free of PCR inhibitors extremely challenging (Monteiro et al., *J Clin Microbiol.* 35(4):995-998 (1997)). Furthermore, the presence of RNases and DNases in stool poses a logistical problem in the form of nucleic acid degradation that occurs during sample collection and transport (Nechvatal et al., *J Microbiol Meth.* 72: 124-132 (2008)). Current techniques require either freezing or the introduction of preservatives to stool samples to preserve the nucleic acids of pathogenic microbes within the sample.

The present disclosure provides methods for determining whether a patient suffering from acute gastroenteritis will benefit from treatment with therapeutic agents that inhibit Norovirus genogroup I (GI) or Norovirus genogroup II (GII), and are based on detecting Norovirus genogroup I (GI) and Norovirus genogroup II (GII) in a stool sample by assaying for the presence of Norovirus genogroup I (GI) and Norovirus genogroup II (GII) target nucleic acids using real-time RT-PCR. The disclosed methods comprise: (a) contacting the stool sample with: (i) a first primer pair that specifically hybridizes to a Norovirus genogroup I (GI) target nucleic acid sequence, if present; and (ii) a second primer pair that specifically hybridizes to a Norovirus genogroup II (GII) target nucleic acid sequence, if present, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample; (b) subjecting the reaction-sample mixture to real-time RT-PCR conditions under which each of the target nucleic acids present in the stool sample is amplified to produce a fluorescent signal; (c) detecting the amount of fluorescent signal produced by each fluorophore using an integrated thermal cycling system; and (d) determining the presence of one or more of Norovirus genogroup I (GI) and Norovirus genogroup II (GII) in the stool sample by comparing the amount of fluorescence generated by the target nucleic acids. Kits for use in practicing the methods are also provided.

Definitions

Unless otherwise defined, all technical and scientific terms used herein have the same meaning as commonly understood by one of ordinary skill in the art to which the present technology belongs.

As used herein, the term "about" in reference to a number is generally taken to include numbers that fall within a range of 1%-10% in either direction (greater than or less than) of the number unless otherwise stated or otherwise evident from the context.

As used herein, the terms "amplify" or "amplification" with respect to nucleic acid sequences, refer to methods that increase the representation of a population of nucleic acid sequences in a sample. Copies of a particular target nucleic acid sequence generated in vitro in an amplification reaction are called "amplicons" or "amplification products". Amplification may be exponential or linear. A target nucleic acid may be DNA (such as, for example, genomic DNA and cDNA) or RNA. While the exemplary methods described hereinafter relate to amplification using polymerase chain reaction (PCR), numerous other methods such as isothermal methods, rolling circle methods, etc., are well known to the skilled artisan. The skilled artisan will understand that these other methods may be used either in place of, or together with, PCR methods. See, e.g., Saiki, "*Amplification of Genomic DNA*" in PCR PROTOCOLS, Innis et al., Eds., *Academic Press, San Diego, CA* 1990, pp 13-20; Wharam, et al., *Nucleic Acids Res.* 29(11):E54-E54 (2001).

An "amplification mixture" as used herein is a mixture of reagents that are used in a nucleic acid amplification reaction, but does not contain primers or sample. An amplification mixture comprises a buffer, dNTPs, and a DNA polymerase. An amplification mixture may further comprise at least one of $MgCl_2$, KCl, nonionic and ionic detergents (including cationic detergents).

An "amplification master mix" comprises an amplification mixture and primers for amplifying one or more target nucleic acids, but does not contain the sample to be amplified.

The terms "complement", "complementary" or "complementarity" as used herein with reference to polynucleotides (i.e., a sequence of nucleotides such as an oligonucleotide or a target nucleic acid) refer to the Watson/Crick base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

As used herein, a "cycle threshold" (Ct) for an analyte is the PCR cycle at which the fluorescence signal crosses a specified fluorescence threshold. The Ct depends on the amplification reaction efficiency which includes starting template copy number, organism lysis, PCR amplification, hybridization or cleavage of a fluorogenic probe and sensitivity of detection. The Ct provides a relative measure of the concentration of the target nucleic acid in the PCR reaction. Many factors other than the concentration of the target nucleic acid can impact the absolute value of Ct. However, artifacts from the reaction mix or instrument that change the fluorescence measurements associated with the Ct calculation will result in template-independent changes to the Ct value.

As used herein, the term "detecting" refers to determining the presence of a target nucleic acid in the sample. Detection does not require the method to provide 100% sensitivity and/or 100% specificity.

As used herein, the term "direct amplification" refers to a nucleic acid amplification reaction in which the target nucleic acid is amplified from the sample without prior purification, extraction, or concentration.

As used herein, the term "extraction" refers to any action taken to remove nucleic acids from other (non-nucleic acid) material present in the sample. The term extraction includes mechanical or chemical lysis, addition of detergent or protease, or precipitation and removal of non-nucleic acids such as proteins.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" can be an individual organism, a vertebrate, a mammal, or a human. In a preferred embodiment, the individual, patient or subject is a human.

As used herein, the term "multiplex PCR" refers to the simultaneous generation of two or more PCR products or amplicons within the same reaction vessel. Each PCR product is primed using a distinct primer pair. A multiplex reaction may further include specific probes for each product that are labeled with different detectable moieties.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides that function as primers or probes are generally at least about 10-15 nucleotides in length or up to about 70, 100, 110, 150 or 200 nucleotides in length, and more preferably at least about 15 to 25 nucleotides in length. Oligonucleotides used as primers or probes for specifically amplifying or specifically detecting a particular target nucleic acid generally are capable of specifically hybridizing to the target nucleic acid.

A "positive control nucleic acid" or "internal positive amplification control" as used herein is a nucleic acid known to be present in a sample at a certain amount or level. In some embodiments, a positive control nucleic acid is not naturally present in a sample and is added to the sample prior to subjecting the reaction-sample mixture to real-time RT-polymerase chain reaction as disclosed in the methods of the present technology for detecting the presence of a Norovirus genogroup in a sample.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of double-stranded DNA (dsDNA) or cDNA. A "reverse primer" anneals to the sense-strand of dsDNA or RNA.

Primers are typically at least 10, 15, 18, or 30 nucleotides in length or up to about 100, 110, 125, or 200 nucleotides in length. In some embodiments, primers are preferably between about 15 to about 60 nucleotides in length, and most preferably between about 25 to about 40 nucleotides in length. In some embodiments, primers are 15 to 35 nucleotides in length. There is no standard length for optimal hybridization or polymerase chain reaction amplification. An optimal length for a particular primer application may be readily determined in the manner described in H. Erlich, *PCR Technology*, PRINCIPLES AND APPLICATION FOR DNA AMPLIFICATION, (1989).

A "primer extension reaction" refers to a synthetic reaction in which an oligonucleotide primer hybridizes to a target nucleic acid and a complementary copy of the target nucleic acid is produced by the polymerase-dependent 3'-addition of individual complementary nucleotides. In some embodiments, the primer extension reaction is PCR.

As used herein, the term "primer pair" refers to a forward and reverse primer pair (i.e., a left and right primer pair) that can be used together to amplify a given region of a nucleic acid of interest.

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be used to detect the presence or absence of a methylated target nucleic acid. Probes are typically at least about 10, 15, 20, 25, 30, 35, 40, 50, 60, 75, 100 nucleotides or more in length.

A "probe element" as used herein refers to a stretch of nucleotides that (a) is associated with a primer in that it is connected to or located adjacent to the primer nucleic acid sequence, and (b) specifically hybridizes under stringent conditions to a target nucleic acid sequence to be detected.

As used herein, the term "primer-probe detection system" refers to a method for real-time PCR. This method utilizes a bi-functional molecule (referred to herein as a primer-probe), which contains a PCR primer element covalently linked by a polymerase-blocking group to a probe element. Additionally, each primer-probe molecule contains a fluorophore that interacts with a quencher to reduce the background fluorescence. In some embodiments, primer-probes may comprise a 3' primer with a 5' extended probe tail comprising a hairpin structure which possesses a fluorophore/quencher pair. During PCR, the polymerase is blocked from extending into the probe tail by the inclusion of hexethylene glycol (HEG). During the first round of amplification the 3' target-specific primer anneals to the target nucleic acid and is extended such that the primer-probe is now incorporated into the newly synthesized strand, which possesses a newly synthesized target region for the 5' probe. During the next round of denaturation and annealing, the probe region of the primer-probe hairpin loop will hybridize to the target, thus separating the fluorophore and quencher and creating a measurable signal. Such primer-probes are described in Whitcombe et al., *Nature Biotech* 17: 804-807 (1999). SCORPION primers are exemplary primer-probes.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Forster or fluorescence resonance energy transfer ("FRET"). Quenching by FRET is generally used in TaqMan® probes while proximal quenching is used in molecular beacon and Scorpion™ type probes.

A "reaction-sample mixture" as used herein refers to a mixture containing amplification master mix and a sample.

As used herein, the term "sample" refers to clinical samples obtained from a patient or isolated microorganisms. In preferred embodiments, a sample is obtained from a biological source (i.e., a "biological sample"), such as tissue, bodily fluid, or microorganisms collected from a subject. Sample sources include, but are not limited to, stool, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include unformed or formed stool samples. Unformed stool refers to feces that are soft and shapeless. Formed stool refers to feces that are solid, firm, bulky and lubricated. In some embodiments, the sample is a rectal swab stored in liquid Amies media.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include at least 50, 60, 70, 80, 90, 95, 98, and 99%.

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include at least 50, 60, 70, 80, 90, 95, 98, and 99%.

The term "stringent hybridization conditions" as used herein refers to hybridization conditions at least as stringent as the following: hybridization in 50% formamide, 5×SSC, 50 mM $NaH_2PO4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein "TaqMan® PCR detection system" refers to a method for real-time PCR. In this method, a TaqMan® probe which hybridizes to the amplified nucleic acid segment is included in the amplification master mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

The terms "target nucleic acid" or "target sequence" as used herein refer to a nucleic acid sequence of interest to be detected and/or quantified in the sample to be analyzed. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion, insertion or duplication, tandem repeat elements, a gene of interest, a region of a gene of interest or any upstream or downstream region thereof. Target nucleic acids may represent alternative sequences or alleles of a particular gene. Target nucleic acids may be derived from genomic DNA, cDNA, or RNA.

Biological Sample Collection and Preparation

Isolating viral nucleic acids from complex samples such as formed or unformed stool matrices by extracting total nucleic acids (e.g., by a non-specific precipitation method) can be challenging because total nucleic acids isolated from a stool sample comprises biological interferents such as nucleic acids from the gut-resident bacteria along with nucleic acids from the subject. Moreover, conventional methods and kits are primarily designed to prepare DNA or RNA from small samples, e.g., samples having masses of less than 1 gram, e.g., 50 to 200 milligrams, limiting the yield of target nucleic acid from complex samples to very small amounts. Additional drawbacks are that most conventional techniques do not effectively remove PCR inhibitors and often require long processing steps, e.g., incubations. Using a conventional method or kit to attain the starting quantities needed to attain high detection sensitivity requires multiple DNA extractions (e.g., the use of multiple kits) from multiple samples in addition to extra purification steps to remove inhibitors.

The methods and compositions of the present technology are useful in detecting Norovirus genogroup I (GI) and Norovirus genogroup II (GII) in a stool sample obtained from a subject without extracting viral nucleic acids from the stool sample prior to performing real-time RT-PCR, and circumvent the need for freezing or adding preservatives to the collected stool samples to prevent degradation of viral nucleic acids in the stool samples.

The methods disclosed herein are useful in detecting Norovirus genogroups (GI and GII) in biological samples derived from sterile and/or non-sterile sites. "Sterile sites" include body fluids such as whole blood, plasma, cell free plasma, urine, cerebrospinal fluid, synovial fluid, pleural fluid, pericardial fluid, intraocular fluid, tissue biopsies or endrotracheal aspirates. As used herein, "cell-free plasma" refers to plasma containing less than 1% cells by volume. "Non-sterile sites" include sputum, stool, skin swabs, inguinal swabs, nasal swabs and throat swabs. In some embodiments, the biological samples comprise formed or unformed stool samples or a rectal swab stored in liquid Amies media. In other embodiments, the biological samples comprise viral cultures. Samples may also include viral isolates.

A biological stool sample may be suspected of containing Norovirus genogroups (GI and GII) and/or nucleic acids of one or more Norovirus genogroups (GI and GII). In addition, a biological stool sample may be obtained from a subject suspected of being infected with one or more Norovirus genogroups (GI and GII). The biological stool sample may be contacted with an amplification master mix for use in a microfluidic/microelectronic centrifugation platform.

Although the disclosed methods preferably employ unprocessed biological stool samples thus resulting in a direct, streamlined sample-to-result process, the detection methods disclosed herein will be effective if used on isolated nucleic acid (DNA or RNA) purified from a biological stool sample according to any methods well known to those of skill in the art. If desired, the stool sample may be collected or concentrated by centrifugation and the like. The cells of the sample may be subjected to lysis, such as by treatments with enzymes, heat surfactants, ultrasonication or a combination thereof. Alternatively, a biological stool sample may be processed using a commercially available nucleic acid extraction kit.

In some embodiments, one or more primer pairs are present in an amplification master mix that further comprises DNA polymerase, dNTPs and PCR buffer prior to contact with the biological stool sample. Amplification of the Norovirus genogroup (e.g., GI and GII) target nucleic acids preferably occurs in a multiplex format. Alternatively, individual PCR reactions for each multicopy insertion sequence may also be used. The biological stool sample may be contacted with the primer pair(s) and/or with an amplification master mix to form a reaction-sample mixture in a direct amplification disc. For example, the biological stool sample may be contacted with the amplification master mix in a direct amplification disc such as the Direct Amplification Disc marketed by Focus Diagnostics, Inc. (Cypress, Calif., USA) as part of the SIMPLEXA™ Direct real-time RT-PCR assays to work in concert with the Integrated Cycler System. A direct amplification disc is a thin, circular disc containing multiple designated regions, each of which contains a well for receiving an amplification master mix and an associated well for receiving unprocessed patient sample. The sample-reaction mixture is produced in the direct amplification disc upon or after addition of the amplification master mix and the sample.

Real-Time PCR

Amplification of target nucleic acids can be detected by any of a number of methods well-known in the art such as gel electrophoresis, column chromatography, hybridization with a probe, sequencing, melting curve analysis, or "real-time" detection.

For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, Scorpion™ primer system and use of intercalating dyes for double-stranded nucleic acid.

In real-time quantitative PCR, the accumulation of amplification product is measured continuously in both standard dilutions of target DNA and samples containing unknown amounts of target DNA. A standard curve is constructed by correlating initial template concentration in the standard samples with the number of PCR cycles (Ct) necessary to produce a specific threshold concentration of product. In the test samples, target PCR product accumulation is measured after the same Ct, which allows interpolation of target DNA concentration from the standard curve.

In some embodiments, amplified nucleic acids are detected by hybridization with a specific probe. Probe oligonucleotides, complementary to a portion of the amplified target sequence may be used to detect amplified fragments. In some embodiments, hybridization may be detected in real-time. In an alternate embodiment, hybridization is not detected in real-time. Amplified nucleic acids for each of the target sequences may be detected simultaneously (i.e., in the same reaction vessel such as multiplex PCR) or individually (i.e., in separate reaction vessels). In certain embodiments, multiple target nucleic acids are detected simultaneously, using two or more distinguishably-labeled (e.g., via different detectable moieties such as color), gene-specific oligonucleotide probes, one which hybridizes to the first target sequence and the other which hybridizes to the second target sequence.

In some embodiments, the different primer pairs are labeled with different distinguishable detectable moieties. Thus, for example, HEX and FAM fluorescent dyes may be present on different primer pairs in the multiplex PCR and associated with the resulting amplicons. In other embodiments, the forward primer is labeled with one detectable moiety, while the reverse primer is labeled with a different detectable moiety, e.g. FAM dye for a forward primer and HEX dye for a reverse primer. Use of different detectable moieties is useful for discriminating between amplified products which are of the same length or are very similar in length.

For sequence-modified nucleic acids, the target may be independently selected from the top strand or the bottom strand. Thus, all targets to be detected may comprise top strand, bottom strand, or a combination of top strand and bottom strand targets.

One general method for real-time PCR uses fluorescent probes such as the TaqMan® probes, molecular beacons, and Scorpion primer-probes. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

Real-time PCR is performed using any suitable instrument capable of detecting the accumulation of the PCR amplification product. Most commonly, the instrument is capable of detecting fluorescence from one or more fluorescent labels. For example, real-time detection on the instrument (e.g., an ABI Real-Time PCR System 7500@ sequence detector) monitors fluorescence and calculates the measure of reporter signal, or Rn value, during each PCR cycle. The threshold cycle, or Ct value, is the cycle at which fluorescence intersects the threshold value. The threshold value can be determined by the sequence detection system software or manually.

In some embodiments, the probes employed are detectably labeled and the detecting is accomplished by detecting the probe label for each amplification product. A quencher may further be associated with the detectable label which prevents detection of the label prior to amplification of the probe's target. TaqMan® probes are examples of such probes.

TaqMan® probes (Heid et al., *Genome Res.* 6: 986-994, 1996) use the fluorogenic 5' exonuclease activity of Taq polymerase to measure the amount of target sequences in DNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase replicates a template on which a TaqMan® probe is bound, its 5' exonuclease activity cleaves the probe. This terminates the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye. If the quencher is an acceptor fluorophore, then accumulation of PCR product can be detected by monitoring the decrease in fluorescence of the acceptor fluorophore.

In certain embodiments, real-time PCR is performed using a bifunctional primer-probe detection system (e.g., Scorpion™ primers). With Scorpion primers, sequence-specific priming and PCR product detection is achieved using a single molecule. The Scorpion primer maintains a stem-loop configuration in the unhybridized state. The fluorophore is attached to the 5' end and is quenched by a moiety coupled to the 3' end, although in certain embodiments, this arrangement may be switched. The 3' portion of the stem and/or loop also contains sequence that is complementary to the extension product of the primer and is linked to the 5' end of a specific primer via a non-amplifiable monomer. After extension of the primer moiety, the specific probe sequence is able to bind to its complement within the extended amplicon, thus opening up the hairpin loop. This prevents the fluorescence from being quenched and a signal is observed. A specific target is amplified by the reverse primer and the primer portion of the Scorpion™ primer, resulting in an extension product. A fluorescent signal is generated due to the separation of the fluorophore from the quencher resulting from the binding of the probe element of the Scorpion™ primer to the extension product.

In some embodiments, the probes employed in the disclosed methods comprise or consist of short fluorescently labeled DNA sequences designed to detect sections of DNA sequence with a genetic variation such as those disclosed in French et al., *Mol Cell Probes,* 5(6):363-74 (2001), incorporated by reference herein in its entirety. HyBeacons® are an example of this type of probe.

In some embodiments of the method, at least one primer of each primer pair or at least one probe in the amplification reaction comprises a detectable moiety. Alternatively, the detectable moiety may be on a probe that is attached to the primer, such as with a primer-probe. In some embodiments, the detectable moiety or label is a fluorophore. Suitable fluorescent moieties include, but are not limited to the following fluorophores: 4-acetamido-4'-isothiocyanatostilbene-2,2'disulfonic acid, acridine and derivatives (acridine, acridine isothiocyanate), Alexa Fluors (Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes)), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY® R-6G, BOPIPY® 530/550, BODIPY® FL, Brilliant Yellow, Cal Fluor Red 610® (CFR610), coumarin and derivatives (coumarin, 7-amino-4-methylcoumarin (AMC, Coumarin 120), 7-amino-4-trifluoromethylcoulurain (Coumarin 151)), Cy2®, Cy3®, Cy3.5®, Cy5®, Cy5.5®, cyanosine, 4',6-diaminidino-2-phenylindole (DAPI), 5', 5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET), fluorescamine, IR144, IR1446, lanthamide phosphors, Malachite Green isothiocyanate, 4-methylumbelliferone, ortho cresolphthalein, nitrotyrosine, pararosaniline, Phenol Red, B-phycoerythrin, R-phycoerythrin, allophycocyanin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives, Quasar 670®, and VIC®.

Suitable quenchers are selected based on the fluorescence spectrum of the particular fluorophore. Useful quenchers include, for example, the Black Hole™ quenchers BHQ-1, BHQ 2, and BHQ-3 (Biosearch Technologies, Inc.), and the ATTO-series of quenchers (ATTO 540Q, ATTO 580Q, and ATTO 612Q; Atto-Tec GmbH).

In some embodiments of the method, the reaction-sample mixture is subjected to real-time RT-PCR conditions under which each of the target nucleic acids present in the biological sample is amplified and the amplified product(s) are detected and measured. In some embodiments, the biological sample is loaded directly into a direct amplification disc without a separate, front-end specimen preparation, followed by Real-time RT-PCR detection and differentiation of target analytes in the same disc. In certain embodiments, the amplification is performed in a Direct Amplification Disc (an 8-well disc from Focus Diagnostics, Inc.). In some embodiments, real-time RT-PCR amplification is performed using the SIMIPLEXA™ Direct assay in a direct amplification disc and detection is performed using an integrated thermal cycler such as the Integrated Cycler sold by Focus Diagnostics (Cypress, CA, USA). The Integrated Cycler can receive a Direct Amplification Disc and is capable of performing multiple assays per disc. This apparatus can heat at >5° C. per second and cool at >4° C. per second. Cycling parameters can be varied, depending on the length of the amplification products to be extended. In certain embodiments, an internal positive amplification control (IPC) can be included in the sample, utilizing oligonucleotide primers, probes and/or primer-probes.

Alternate Methods of Detecting Target Nucleic Acids

Alternatively, detection of the target nucleic acids can occur by measuring the end-point of the reaction. In end-point detection, the amplicon(s) could be detected by first size-separating the amplicons, and then detecting the size-separated amplicons. The separation of amplicons of different sizes can be accomplished by gel electrophoresis, column chromatography, capillary electrophoresis, or other separation methods known in the art.

The detectable label can be incorporated into, associated with or conjugated to a nucleic acid. Label can be attached by spacer arms of various lengths to reduce potential steric hindrance or impact on other useful or desired properties. See, e.g., Mansfield, 9 *Mol. Cell. Probes* 145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

Examples of other useful labels that aid in the detection of target nucleic acids include radioisotopes (e.g., $^{32}$P, $^{3}$S, $^{3}$H, $^{1}$C, $^{125}$I, $^{131}$I), electron-dense reagents (e.g., gold), enzymes (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

In other embodiments, fluorescent nucleotide analogs can be used to label nucleic acids, see, e.g., Jameson, *Methods. Enzymol.* 278: 363-390 (1997); Zhu, *Nucl. Acids Res.* 22: 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

In some embodiments, detectably labeled probes can be used in hybridization assays including, but not limited to Northern blots, Southern blots, microarray, dot or slot blots, and in situ hybridization assays such as fluorescent in situ hybridization (FISH) to detect a target nucleic acid sequence within a biological sample. Certain embodiments may employ hybridization methods for measuring expression of a polynucleotide gene product, such as mRNA. Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y., 1989); Berger and Kimmel Methods in Enzy- Norovirus Screening Assay of the Present Technology In various embodiments of the present disclosure, primers and probes are used in the methods described herein to amplify and detect target nucleic acid sequences of Norovirus genogroup I (GI) and Norovirus genogroup II (GII). In addition, primers can also be used to amplify one or more control nucleic acid sequences. In some embodiments, the control nucleic acid sequence comprises CTCGTCGACAATGGCGGAACTGGCGACGTGACTGTCGCCCCAAGCAACTTCGCTA ACGGGGTCGCTGAA (SEQ ID NO: 12), and a forward primer comprising 5'd CTCGTCGACAATGGCGGAA 3' (SEQ ID NO: 13), a reverse primer comprising 5'd TTCAGCGACCCCGTTAGC 3' (SEQ ID NO: 14) and a detectably labelled nucleic acid probe comprising 5'd GCTTGGGGCGACAGTCACGTCGC 3' (SEQ ID NO: 15) are used to amplify the control nucleic acid sequence.

The primers and probes of the present technology are used in the methods described herein to amplify and detect a Norovirus genogroup I (GI) target nucleic acid comprising a sequence that is at least 80-95% identical to SEQ ID NO: 2 or a complement thereof, and a Norovirus genogroup II (GII) target nucleic acid comprising a sequence that is at least 80-95% identical to SEQ ID NO: 4 or a complement thereof. The target nucleic acids described herein may be detected individually or in a multiplex format, utilizing individual labels for each target.

Specific primers, probes and primer-probes for amplification and detection of all or a fragment of a marker gene specific for Norovirus genogroup I (GI) include those directed to sequences present in Norovirus genogroup I (GI), but absent from other Norovirus genogroups. The detection of a Norovirus genogroup I (GI) target nucleic acid helps to distinguish a sample containing Norovirus genogroup I (GI) from one that may contain another pathogenic Norovirus genogroup, e.g., Norovirus genogroup II (GII). A suitable marker for Norovirus genogroup I (GI) is the gene sequence of Norovirus GI.2 (see, e.g., GenBank Accession No. FJ515294) and is shown below.

```
                                                              (SEQ ID NO: 1)
   1  gtgaatgatg atggcgtcga aagacgtcgt tgcaactaat gttgcaagca acaacaatgc 61  taacaacact agtgctacat ctcgatttt  atcgagattt aagggcttag gaggtggcgc 121  aagccccct  agtcctataa aaattaaaag tacagaaatg gctctgggat taattggcag 181  aacaactcca gaaccaacag ggaccgctgg tccaccgccc aaacaacaga gggaccgacc 241  tcccagaact caggaggagg tccagtatgg tatgggatgg tctgacaggc ccattgatca 301  aaacgttaaa tcatgggaag agcttgatac cacagtcaag gaagagatct tagacaacca 361  caaagagtgg tttgacgctg gtggtttggg tccttgcaca atgcctccaa catatgaacg 421  ggtcagggat gacagtccac ctggtgaaca ggttaaatgg tccgcgcgtg atggagtcaa 481  cattggagtg gagcgcctca caacagtgag tggacccgag tggaaccttt gccctctacc 541  ccccattgac ttaaggaaca tggagccagc cagtgaaccc actattggag atatgataga 601  attctatgaa ggccacatct atcattactc catatacatt gggcaaggca aaacagtcgg 661  tgtccattct ccacaggcag cgttctcagt ggctagggtg accatccagc ccatagccgc 721  ttggtggaga gtttgttaca taccccaacc caagcacaga ctgagttacg accaactcaa 781  ggaattagag aatgagccat ggccatatgc ggccataact aataattgtt ttgaattctg 841  ctgtcaagtc atgaaccttg aggacacgtg gttacagagg cggttgatca cgtcgggtag 901  attccaccac cccacccaat cgtggtcaca gcagacccct gagttccagc aagatagcaa 961  gttagagttg gtcagggatg ctatattagc tgcagtgaat ggtcttgttt cgcagccctt 1021  caagaatttc ttgggtaaac tcaaacctct caatgtgctc aacattttgt ctaattgtga 1081  ttggaccttc atgggagtgg tggagatggt tatactatta cttgaactct ttggcgtgtt 1141  ctggaacccg cctgatgtgt ccaattttat agcgtccctt ctccctgatt tccatcttca 1201  aggacctgaa gacttggcac gagatctagt cccagtgatt cttggcggca taggattggc 1261  catcgggttc accagagaca aagttacaaa ggttatgaag agtgctgtgg atggtcttcg 1321  agctgctaca caactgggac aatatgggtt agaaatattc tcactactca agaagtattt 1381  ctttgggggg gaccagactg agcgcacccct caaaggcatt gaggcggcag tcatagatat 1441  ggaagtgttg tcctccacat cagtgacaca gctagtgaga gacaaacagg cagcaaaagc
```

```
-continued
1501  ttatatgaac atcttggaca atgaagaaga gaaagccagg aagctctcag ctaaaaacgc
1561  tgacccacat gtgatatcct caacaaatgc cctaatatcg cgtatttcca tggcacgatc
1621  tgcattggcc aaggcccagg ctgagatgac cagtcgaatg agaccagttg ttattatgat
1681  gtgtggcccg cctgggattg ggaagaccaa ggctgctgag cacctagcta agcgtctagc
1741  taatgagatc agacctggtg gtaaggtggg gttggttccc cgtgaagctg tcgaccactg
1801  ggacggttat catggtgagg aagtgatgct gtgggacgac tatggcatga caaaaataca
1861  agatgactgt aataaactcc aagccattgc tgattcggcc ccactcacct taaattgtga
1921  caggattgaa acaaaggaa tgcagttcgt ttcagatgca atagtcatca ctaccaacgc
1981  cccaggcccc gcccctgtgg actttgtcaa ccttggacca gtgtgtagac gggtcgactt
2041  cttggtctac tgctctgccc cagaggtgga acagatacgg agggtcagcc ctggtgatac
2101  atcagcactg aaagactgtt ttaagccaga cttctctcat ttaaaaatgg agctggctcc
2161  acaaggtggg tttgacaatc aagggaacac accgtttggc aaaggcacca tgaagccaac
2221  aaccattaac agacttctca tacaagctgt ggcccttacc atggaaaggc aggatgagtt
2281  tcagttacag gggaagatgt atgactttga tgatgacagg gtgtcagcat tcaccaccat
2341  ggcacgtgat aatggcctgg gcatcttgag catggcaggt ctgggcaaga agctacgtgg
2401  tgttacaacg atggagggct taagaatgc cctaaagggg tacaaaatca atgcgtgcac
2461  aataaaatgg caggccaaag tgtactcact agaatcagat ggcaacagtg tcaacattaa
2521  agaggagagg aacgtcttaa ctcagcaaca acagtcggtg tgtgccgcct ctgtcgcgct
2581  cactcgtctt cgggctgcgc gcgcggtggc atacgcatcg tgcatccaat cggctataac
2641  ttctatacta caaattgctg gctcagccct agtggtcaac agagcagtga agagaatgtt
2701  tggcacgcgc acagccacct tgtccctaga gggccccccc agagaacaca aatgcagggt
2761  ccacatggcc aaggccgcag gaaagggacc tattggccat gatgatgtgg tagaaaagta
2821  tgggctttgc gaaacagagg aggacgaaga agtggcccac gctgaaatcc cttctgctac
2881  catggagggc aagaacaaag ggaagaacaa gaaaggacgt ggtcggagga acaattacaa
2941  cgccttctcc cgcagaggac tcaatgatga agagtacgaa gagtacaaga agatacgcga
3001  ggagaaaggt ggcaactaca gcatacagga gtacctagaa gacagacaaa ggtatgaaga
3061  agagctggca gaggttcaag caggtggaga tggaggaatt ggggaaactg aaatggaaat
3121  ccgccacaga gtgttctaca atccaagag cagaaagcat catcaggaag aacgacgcca
3181  gctagggctg gtgacaggtt ccgacattcg gaagagaaaa ccaatcgact ggacccccac
3241  caagtcagca tgggcagatg atgagcgtga ggtggattac aatgagaaga tcagcttcga
3301  ggcgcccccc actttatgga gtagagtgac aaagtttggg tctggatggg gtttctgggt
3361  cagccctaca gtcttcataa ccacaacgca cgttatacca accagtgcaa aggagttctt
3421  tggtgaaccc ctaaccagca tagctatcca cagggctggt gagttcactc tcttcaggtt
3481  ttcaaagaaa attaggcctg atctcacagg tatgatcctt gaggagggtt gccccgaggg
3541  cacggtgtgt tcagtactaa taaaaaggga ctctggtgaa ctactgccat tggccgtgag
3601  gatgggcgca atagcatcaa tgcgcataca gggccgcctt gtccatgggc aatctggcat
3661  gttactcacc ggggcaaatg ctaagggcat ggaccttgga accatcccag gggattgtgg
3721  ggctccttat gtttataaga gggctaatga ctgggtggtc tgtggtgtac atgccgctgc
3781  caccaagtca ggcaacaccg ttgtgtgcgc cgttcaggcc agtgaaggag aaactacgct
3841  tgaaggcggt gacaaaggtc attatgctgg acatgaaata attaagcatg ttgtggacc
3901  agctctatca accaaaacca aattctggaa atcatccccc gaaccactgc cccctgggt
```

-continued

```
3961  ctacgagccc gcctacctcg ggggccggga ccctaggggtg tctggcggtc cctcactcca
4021  acaagtgttg cgggatcagt taaagccatt tgctgagcca cgaggacgta tgccagaacc
4081  aggtctcttg gaggccgcag ttgagactgt gacttcatca ttagagcagg ttatggacac
4141  tcccgttcct tggagctata gtgatgcgtg ccagtccctt gacaagacca ctagttctgg
4201  tttcccctac catagaagga agaatgacga ctggaatggc accacctttg ttagggagtt
4261  aggggagcag gcggcacacg ctaataacat gtatgagcag gctaaaagta tgaaacccat
4321  gtacacggca gcacttaaag atgaactagt caaaccagag aaagtatacc agaaagtgaa
4381  aaagcgcttg ttatggggag cagacttggg cacggtagtt cgggccgcac gggcttttgg
4441  cccattctgt gatgctataa aatcccacac aatcaaattg cctatcaaag ttggaatgaa
4501  ttcaattgag gatggaccac tgatctatgc agaacattcg aaatataagt accattttga
4561  tgcagattac acagcttggg attcaactca aaataggcaa atcatgacag agtcattttc
4621  aatcatgtgt cggctaactg catcacctga attagcttca gtggtggctc aagacttgct
4681  cgcaccttca gagatggatg ttggtgacta cgtcataaga gtgaaggaag gtctcccatc
4741  tggtttccca tgcacatcac aagttaatag cataaaccat tggttaataa ctctgtgtgc
4801  cctttctgaa gtaactggtc tgtcgccaga tgttatccag tctatgtcat atttctcttt
4861  ctatggtgat gatgaaatag tgtcaactga catagaattt gatccagcaa aactaacaca
4921  agttctcaga gagtatggac ttaaacccac ccgccccgac aaaagcgagg cccaataat
4981  tgtaaggaag aatgtggatg gtttggtctt tttacgtcgc actatctccc gtgacgctgc
5041  gggattccaa ggacgactgg accgagcatc cattgagaga caaatctact ggactagagg
5101  acccaaccat tcagaccctt tgagaccct ggtgccacac caacaaagga aggtccaact
5161  aatatcatta ttgggcgagg cctcactgca tggtgaaaag ttttacagga agatttcaag
5221  caaagttatc caggaaatta aaacaggggg tcttgaaatg tatgtgccag gatggcaagc
5281  catgttccgt tggatgcggt tccatgacct tggtttgtgg acaggagatc gcaatctcct
5341  gcccgaattt gtaaatgatg atggcgtcta aggacgcccc tcaaagcgct gatggcgcaa
5401  gcggcgcagg tcaactggtc ccggaggtta atacagctga ccccttaccc atggaacccg
5461  tggctgggcc aacaacagcc gtagccactg ctgggcaagt taatatgatt gatccctgga
5521  ttgttaataa ttttgtccag tcaccgcaag gtgagtttac aatttcccct aataatccc
5581  ccggtgatat tttgtttgat ctacaattag gtccacattt aaacccttc ttgtcacatt
5641  tgtcccaaat gtataatggc tgggttggaa acatgagagt taggattctc cttgctggga
5701  atgcattctc agccggaaag attatagtct gttgtgtccc cctggcttc acatcttcct
5761  ctctcaccat agctcaggct acattgtttc ccatgtgat tgctgatgtg agaacccttg
5821  aaccaataga aatgcccctc gaggacgtgc gcaatgtcct ctatcacacc aatgataatc
5881  aaccaacaat gcggctggtg tgtatgctgt acacgccgct ccgcactggt gggggtctg
5941  gtaattctga ttctttgta gttgctggca gggtgctcac ggcccctagt agcgacttca
6001  gtttcttgtt ccttgtcccg cctaccatag aacagaagac tcgggctttt actgtgccca
6061  atatcccctt gcaaaccta tccaattcta ggtttccttc cctcatccag gggatgattc
6121  tgtcccctga cgcatctcaa gtggtccaat tccaaaatgg acgttgtctt atagatggtc
6181  aactcctagg cactacaccc gccacatcag acagctgtt cagagtgaga ggaaagataa
6241  atcagggagc ccgcacactc aatctcacag aggtggatgg caagccattc atggcatttg
6301  attcccctgc acctgtgggg ttccccgatt ttggaaaatg tgattggcac atgagaatca
```

```
6361 gcaaaacccc aaataacaca agctcaggtg accctatgcg cagtgtcgac gtgcaaaccg
6421 atgtgcaggg ttttgtgcca cacctgggaa gcatacagtt tgatgaagtg ttcaaccatc
6481 ccacaggtga ctacattggc accattgaat ggatttccca gccatctaca cccctggaa
6541 cagatattaa tttatgggag atccccgatt atggatcatc cctctcccaa gcagctaatc
6601 tggccccccc agtattcccc cctggatttg gtgaggctct tgtgtacttt gtttctgctt
6661 ttccaggccc caacaaccgc tcagcccga atgatgtgcc ttgtctcctc cctcaagagt
6721 acgtaaccca ctttgtcagt gaacaagccc caacgatggg tgacgcagct ttgctgcatt
6781 atgtcgaccc tgataccaac agaaaccttg gggagttcaa gttataccct ggaggttacc
6841 tcacctgtgt accaaacggg gtgggtgccg ggcctcaaca gcttcccctt aatggtgtct
6901 ttctctttgt ctcttgggtg tctcgttttt atcagctcaa gcctgtggga acagccagta
6961 cggcaagagg taggcttgga gtgcgccgta tataatggcc caagccatta taggagcaat
7021 tgccgcgtca gctgctggct cagcattggg tgcgggcatc caggctggtg ccgaagctgc
7081 gcttcagagt cagagatacc aacaagactt agccctgcaa aggaatacct ttgaacatga
7141 taaagatatg ctttcctacc aggttcaggc aagtaatgcg ctcttagcaa agaatctcaa
7201 tacccgctat tctatgctta ttgcaggagg tctttctaat gctgatgctt ctcggctgt
7261 tgctggagcc ccagtaacac aattgattga ttggaacggc actcgtgttg ctgcccccag
7321 atcagatgca acaactctga ggtctggtgg ttttatggca gtccccatgc ctgttcaacc
7381 caaatctaag gccccgcaat cctctgggtt ctctaatcct gcttatgata tgtccacagt
7441 ttcctctagg acttcttcct gggtgcagtc acagaattcc ctgcgaaatg tgtcaccatt
7501 ccataggcag gccctgcaga ctgtatgggt cactccacct gggtctactt cttcttcttc
7561 tgtttcctca cacccttatg gtgttttaa tacggatagg atgccgctat tcgcaaattt
7621 gcggcgctaa tgttgtaata taatgcagca gtgggcacta tattcaattt ggtttaatta
7681 gtaaataatt tggctattg
```

The nucleic acid sequence of the Norovirus genogroup I (GI) amplicon generated using the methods disclosed herein is double-underlined, and is represented as SEQ ID NO: 2.

In some embodiments, the target nucleic acid corresponds to nucleotides 5288-5374 of SEQ ID NO: 1 (i.e., SEQ ID NO: 2) or a fragment thereof. Exemplary primer and labeled probe sequences for amplifying and detecting the Norovirus genogroup I (GI) target nucleic acid sequence include:

```
Fwd primer    5'd CGYTGGATGCGITTYCATGA 3'
              (SEQ ID NO: 5)

Rev primer    5'd TCCTTAGACGCCATCATCATTTAC 3'
              (SEQ ID NO: 6)

Probe 1       5'd TGGACAGGAGAYCGCIATCTCYTGCCCGA 3'
              (SEQ ID NO: 7)

Probe 2       5'd TGGACAGGAGATCGCAATCTACTGCCTGA 3'
              (SEQ ID NO: 8)
```

A suitable marker for Norovirus genogroup II (GII) is the gene sequence of Norovirus Hu/Houston/TCH186/2002/US provided at Genbank Accession No. EU310927 and is shown below.

```
                                                          (SEQ ID NO: 3)
   1 gtgaatgaag atggcgtcta acgacgcttc cgctgccgct gttgctaaca gcaacaacga
  61 caccgcaaaa tcttcaagtg acggagtgct ttctagcatg gctgtcactt ttaaacgagc
 121 cctcggggcg cggcctaaac agcccccccc gagggaaata ccacaaagac ccccacgacc
 181 acctactcca gaactggtca aaaagatccc ccctcccccg cctaacggag aggatgagat
 241 agtggtttct tatagtgtca agatggtgt ttccggtttg cctgagcttt ccaccgtcag
 301 gcaaccggaa gaagctaata cggccttcag tgtccccca ctcaatcaga gggagaatag
 361 agatgctaag gagccactga ctggaacaat tctggaaatg tgggatggag aaatctacca
```

-continued

```
 421   ttatggcctg tatgtggagc gaggtcttgt actaggtgtg cacaagccac cagctgccat
 481   tagcctcgcc aaggtcgaac taacaccact ctccttgttc tggagacctg tgtatactcc
 541   tcagtacctc atctctccag acactctcaa gaaattacat ggagaaacgt ttccctacac
 601   agcctttgac aacaattgct atgcctttg ttgctgggtc ctggacctaa acgactcgtg
 661   gctgagtagg agaatgatcc agagaacaac tggcttcttc agaccctacc aagattggaa
 721   taggaaaccc ctccccacta tggatgattc caaattaaag aaggtagcta acatattcct
 781   gtgtgccctg tcttcgctat tcaccaggcc cataaaagac ataataggga agctaaggcc
 841   tcttaacatc ctcaacatct tggcttcatg tgattggact ttcgcaggca tagtggagtc
 901   cttgatactc ttggcagagc tctttggagt tttctggaca cccccagatg tgtctgcgat
 961   gattgccccc ttactcggtg attacgagtt gcaaggacct gaagaccttg cagtggagct
1021   cgtccctgta gtgatggggg gaattggtct ggtgctggga ttcaccaaag agaagattgg
1081   aaaaatgttg tcatctgctg catccacctt gagggcttgt aaagatcttg gtgcatatgg
1141   gctagagatc ctaaagttgg tcatgaagtg gttcttcccg aagaagagg aagcaaatga
1201   actggctatg gtgagatcca tcgaggatgc agtgttggac ctcgaggcaa tcgaaaacaa
1261   ccatatgacc accttgctca aggacaaaga tagtctggca acctacatga gaacccttga
1321   cctcgaggaa gagaaagcca gaaaactctc aaccaagtct gcttcacctg acatcgtggg
1381   cacaatcaac gccctttggg cgagaatcgc tgctgcacgt tccctggtgc atcgagcgaa
1441   ggaggaactt tccagcagac caagacctgt agtcttaatg atatcaggca gaccaggaat
1501   agggaagacc caccttgcta gggaagtggc taagagaatc gcagcctccc tcaggagaa
1561   ccagcgtgta ggcctcgtcc cacgcaatgg cgtcgatcac tgggatgcgt acaaggggga
1621   gagggtcgtc ctatgggacg actatggaat gagcaatccc atccacgacg ccctcaggtt
1681   gcaagaactc gctgacactt gcccccctcac tctaaactgt gacaggattg agaataaagg
1741   aaaggttttt gacagcgatg tcatcattat cactactaat ctagctaacc cagcaccact
1801   ggactatgtc aactttgaag catgctcgag gcgtatcgat ttcctcgtgt atgcagaagc
1861   ccctgaagtc gaaaaggcga agcgtgactt cccaggccaa cctgacatgt ggaagaacgc
1921   ttttagttct gatttctcac acataaaact gacactggct ccacagggtg gctttgataa
1981   gaacgggaac accccacacg ggaagggcgt catgaagact ctcactaccg gctcccttat
2041   tgcccgggca tcagggctac tccatgagag gctagatgaa tttgaactac agggcccaac
2101   tctcaccacc ttcaactttg atcgcaacaa agtgcttgcc tttaggcagc ttgctgctga
2161   aaacaaatat gggttgatgg acacaatgaa agttgggagg cagctcaagg atgtcagaac
2221   catgccagaa cttaaacaag cactcaagaa tatctcaatc aagaagtgcc agatagtgta
2281   cagtggttgc acctacacac ttgagtctga tggcaagggc aatgtgaaag ttgacagagt
2341   tcagagcgcc tccgtgcaga ccaacaatga gctgactggc ccctgcacc acctaaggtg
2401   cgccagaatc aggtactatg tcaggtgtgt tcaggaggcc ctgtattcca tcatccagat
2461   tgctgggccc gcatttgtca ccacgcgcat cgtcaagcgt atgaacatac aagacctatg
2521   gtccaagcca caagtggaaa acacagagga ggctaccaac aaggacgggt gcccaaaacc
2581   cagagatgat gaggagttcg tcatttcgtc cgacgacatt aaaactgagg taagaaagg
2641   gaagaacaag accggccgtg gcaagaaaca cacagccttc tcaagcaaag gtctcagtga
2701   tgaggagtac gatgagtaca agaggattag agaagaaagg aatggcaagt actccataga
2761   agagtacctt caggacaggg acaaatacta tgaggaggtg gccattgcca gggcgaccga
2821   ggaagacttc tgtgaagagg aggaggccaa gatccggcaa aggatcttca ggccaacaaa
```

-continued

```
2881  gaaacaacgc aaggaagaaa gagcttctct cggtttggtc acaggttctg aaattaggaa
2941  aagaaaccca gatgatttca agcccaaggg gaaactgtgg gctgacgatg acagaagtgt
3001  ggactacaat gagaaactca gttttgaggc cccaccaagc atctggtcga ggatagtcaa
3061  ctttggttca ggttggggct tctgggtctc ccccagtctg ttcataacat caacccacgt
3121  cataccccag ggcgcaaagg aattctttgg agtccccatc aaacaaattc aggtacacaa
3181  gtcaggcgaa ttctgtcgct tgagattccc gaaaccaatc aggactgatg tgacgggcat
3241  gatcttagaa gaaggtgcgc ccgaaggcac cgtggtcaca ctactcatca aaaggtctac
3301  tggagaactc atgcccctag cagctagaat ggggacccat gcaaccatga aaattcaagg
3361  gcgcactgtt ggaggtcaaa tgggcatgct tctgacagga tccaatgcca aaagcatgga
3421  tctaggcacc acaccaggtg attgcggctg tccctacatc tacaagagag gaaatgacta
3481  tgtggtcatt ggagtccaca cggctgccgc tcgtggggga aacactgtca tatgtgccac
3541  tcaggggagt gaggggggagg ctacacttga aggtggtgac agtaagggaa catattgtgg
3601  tgcgccaatc ctaggcccag ggagtgcccc aaaacttagc accaaaacca aattctggag
3661  atcgtccaca gcaccactcc cacctggcac ctatgaacca gcctatcttg tggcaagga
3721  ccccagagtc aagggtggcc cttcgttgca gcaagtcatg agggatcagc tgaaaccatt
3781  tacagagccc aggggtaagc caccaaagcc aagtgtgtta gaagctgcca agaaaaccat
3841  catcaatgtc cttgaacaaa caattgaccc acctgagaaa tggtcgttcg cacaagcttg
3901  cgcgtccctc gacaagacca cttctagtgg ccatccgcac cacatgcgga aaaacgactg
3961  ctggaacggg gaatccttca caggcaagct ggcagaccag gcttccaagg ccaacctgat
4021  gttcgaagaa gggaagaaca tgacccccagt ctacacaggt gcgcttaagg atgaattagt
4081  caaaactgac aaaatttatg gtaagatcaa gaagaggctt ctctggggtt cggatttagc
4141  gaccatgatc cggtgtgctc gagcattcgg aggcctaatg gatgaactca aagcacactg
4201  tgttacactt cctatcagag ttggtatgaa tatgaatgag gatggcccca tcatcttcga
4261  gaggcattcc aggtacagat accactatga tgctgattac tctcggtggg attcaacaca
4321  acagagagcc gtgttggcag ctgctctaga agtcatggtt aaattctcct cagaaccaca
4381  tttggctcag gtagtcgcag aagaccttct ttctcctagc gtggtggatg tgggtgactt
4441  cacaatatcg atcaacgagg gtcttccctc tggggtgccc tgcacctccc aatggaactc
4501  catcgcccac tggcttctca ctctctgtgc gctctctgaa gttacaaatt tgtccctga
4561  catcatacag gctaattccc acttctcctt ttatggtgat gacgaaattg ttagtacaga
4621  cataaaatta gacccagaga agttgacagc aaaacttaag gaatatggat tgaaaccaac
4681  ccgccctgat aagactgaag gacctcttgt tatctctgaa gacttaaatg gtctgacttt
4741  cctgcggaga actgtgaccc gcgacccagc tggttggttt ggaaaactgg agcagagctc
4801  aatactcagg caaatgtact ggactagagg ccccaaccat gaagacccat ctgaaacaat
4861  gattccacac tcccaaagac ccatacaatt gatgtcccta ctgggagagg ccgcactcca
4921  cggcccaaca ttctacagca aaatcagcaa gttagtcatt gcagagctaa agaaggtgg
4981  tatggatttt tacgtgccca gacaagagcc aa<ins>tgttcaga tggatgagat tctcagatct
5041  gagcacgtgg gagggcgatc gcaatctggc tcccagcttt gtgaatgaag atgcgtcga</ins>
5101  gtgacgccag cccatctgat gggtccacag ccaacctcgt cccagaggtc aacaatgagg
5161  ttatggcttt ggagcccgtt gttggtgccg caattgcggc acctgtagcg ggccaacaaa
5221  atgtaattga cccctggatt agaaataatt ttgtacaagc ccctggtgga gagttcacag
```

```
5281  tatcccctag aaacgctcca ggtgaaatac tatggagcgc gcccttgggc cctgatctga
5341  atccctacct ttctcatttg gccagaatgt acaatggtta tgcaggtggt tttgaagtgc
5401  aggtaattct cgcggggaac gcgttcaccg ccgggaaaat catatttgca gcagtcccac
5461  caaatttccc aactgaaggc ttgagcccca gccaggtcac tatgttcccc catataatag
5521  tagatgttag gcaactggaa cctgtgttga ttcccttacc tgatgtcagg aataatttct
5581  atcactataa tcagtcaaat gaccccacca ttaaactgat agcaatgctg tacacaccac
5641  ttagggctaa taatgctggg gatgatgtct tcacagtctc ttgccgagtc ctcacgaggc
5701  catcccctga ttttgatttt atatttttgg tgccacccac agttgagtca agaaccaaac
5761  cattcaccgt cccaatttta actgttgagg agatgaccaa ttcaagattc cccattcctt
5821  tggaaaagtt gttcacgggt cccagcggtg cctttgttgt tcaaccacaa aatggcagat
5881  gcacgactga tggcgtgctc ttaggtacta cccaactgtc tcctgttaac atctgcactt
5941  tcagagggga tgtcacccac attgcaggca ctcatgatta tacaatgaat ttggcttctc
6001  aaaattggaa caattacgac ccaacagaag aaatcccagc ccctctggga actccagatt
6061  tcgtgggaaa gatccaaggc gtgctcactc aaaccacaag gggagatggc tcgacccgtg
6121  gccacaaagc cacagtgagc actgggagtg tccactttac tccaaagctg ggcagtgttc
6181  aattcaccac tgacacaaac aatgatcttg aaactggcca aaacacgaaa ttcaccccag
6241  tcggtgtcgt ccaggatggt aatagtgccc accaaaatga accccaacaa tgggtgctcc
6301  caaattactc aggtagaact ggccataatg tacacctagc ccctgccgta gcccccactt
6361  ttccgggtga gcaacttctc ttcttcaggt ccactatgcc cggatgcagc gggtatccca
6421  acatgaattt ggattgccta ctcccccagg aatgggtgct gcacttctac caagaggcag
6481  ctccagcaca atctgatgtg gctctgctga gatttgtgaa tccagacaca ggtagggtcc
6541  tgtttgagtg caaacttcat aaatcaggct atgtcacagt ggctcacact ggcccgcatg
6601  atttggtcat ccccccccaat ggctacttca gatttgattc ctgggttaac caattctaca
6661  cgcttgcccc catgggaaat ggagcggggc gtagacgtgc gttataatgg ctggagcttt
6721  ctttgctgga ttggcatctg atgtccttgg ctctggactt ggttccctaa tcaatgctgg
6781  ggctggggcc atcaaccaaa agttgaattt gaaaataac agaaaattgc aacaagcttc
6841  ctttcaattt agcagcaatc tacaacaggc ttccttttcaa catgataaag agatgctcca
6901  agcacaaatt gaggccacta aaaagttgca acagggtatg atggaagtta aacaggcaat
6961  gctcttagag ggtggattct ctgaaacaga tgcagcccgt ggggcaatca acgcccccat
7021  gacaaaggct ttggattgga gcggaacaag gtactgggct cctgatgcta ggactacaac
7081  atacaatgca ggccgctttt ccacccctca accttcgggg gcactgccag gaagaattaa
7141  tcccagggct cctgccccccg ctcagggctc ctccagcaca ccctctagta cttctactgc
7201  tacttctgtg tattcaaatc aaactgtttc aacgagactt ggttctacag ctggttctgg
7261  caccagtgtc tcgagtctcc cgtcaactgc aaggactagg agctgggttg aggatcaaaa
7321  caggaatttg tcacctttca tgagggggggc tcacaacata tcgttcgtca ccccaccatc
7381  tagtagatct tctagccaag gcacagtctc aaccgtgcct aaagaaattt tggactcctg
7441  gactggcgct ttcaacacgc gcaggcagcc tctcttcgct cacattcgta agcgagggga
7501  gtcacggggtg taatgtgaaa agacaaaatt gattatctttt cttttcttta gtgtctttt
```

The nucleic acid sequence of the Norovirus genogroup II (GII) amplicon generated using the methods disclosed herein is underlined, and is represented as SEQ ID NO: 4.

In some embodiments, the target nucleic acid corresponds to nucleotides 5013-5100 of SEQ ID NO: 3 (i.e., SEQ ID NO: 4) or a fragment thereof. Exemplary primer and labeled probe sequences for amplifying and detecting the Norovirus genogroup II (GII) target nucleic acid sedquence include:

| | |
|---|---|
| Fwd primer | 5'd TGTTYAGGTGGATGAGRTTCTCIGA 3' (SEQ ID NO: 9) |
| Rev primer | 5'd TCGACGCCATCTTCATTCACA 3' (SEQ ID NO: 10) |
| Probe | 5'd ACGTGGGAGGGCGATCGCAATCT 3' (SEQ ID NO: 11) |

The norovirus genogroup I (GI) and genogroup II (GII) probe sequences and control probe sequences disclosed herein may be conjugated to a BHQ-1 or BHQ-2 quencher moiety. Further, the norovirus genogroup I (GI) and genogroup II (GII) probe sequences and control probe sequences of the present technology may be detectably labelled with any fluorophore disclosed herein.

Accordingly, qualitative detection and differentiation of Norovirus genogroup I (GI) and Norovirus genogroup II (GII) using the disclosed method may utilize primer pairs, labeled probes and real-time RT-PCR for amplification and detection of the Norovirus genogroup I (GI) and Norovirus genogroup II (GII) target nucleic acid sequences on a direct amplification disc with an integrated cycler system. With this method, target nucleic acid is specifically amplified and simultaneously detected by fluorescent-labeled probes in the same reaction. The probe(s) that specifically hybridizes to the Norovirus genogroup I (GI) target nucleic acid or its complement may comprise a CFR610 label and the probe that specifically hybridizes to the Norovirus genogroup II (GII) target nucleic acid or its complement may comprise a FAM label. The probe that specifically hybridizes to the control target nucleic acid or its complement may comprise a Q670 fluorophore.

Accordingly, in one aspect, the present disclosure provides a method for detecting the presence of at least one Norovirus genogroup in a stool sample comprising: (a) contacting the stool sample with: (i) a first primer pair that amplifies a Norovirus genogroup I (GI) target nucleic acid comprising nucleotides that are at least 80-95% identical to SEQ ID NO: 2 or a complement thereof, and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample; (b) subjecting the reaction-sample mixture to real-time RT-PCR conditions under which each of the target nucleic acids present in the stool sample is amplified to produce a fluorescent signal; (c) detecting the fluorescent signal generated by each amplified target nucleic acid produced in step (b); and (d) detecting the presence of at least one Norovirus genogroup in the stool sample by evaluating the fluorescent signal of each target nucleic acid, wherein detection of the Norovirus genogroup I (GI) target nucleic acid is indicative of the presence of Norovirus genogroup I (GI) in the stool sample; and detection of the Norovirus genogroup II (GII) target nucleic acid is indicative of the presence of Norovirus genogroup II (GII) in the stool sample; and wherein the stool sample is not subjected to an extraction or purification step prior to amplification. Real-time RT-PCR amplification may be performed in a direct amplification disc in concert with an integrated thermal cycler. In some embodiments, Norovirus genogroup I (GI) comprises one or more genotypes selected from the group consisting of GI.1, GI.2, GI.3, GI.4, GI.5, GI.6, GI.7, GI.8, GI.9, GI.10 and GI.14. In certain embodiments, Norovirus genogroup II (GII) comprises one or more genotypes selected from the group consisting of GII.1, GII.2, GII.3, GII.4, GII.5, GII.6, GII.7, GII.8, GII.9, GII.10, GII.11, GII.12, GII.13, GII.14, GII.15, GII.16, GII.17, GII.18, GII.19, GII.20, GII.21, GII.22, and GII.23. In some embodiments, the stool sample comprises unformed stool, formed stool, or a rectal swab stored in liquid Amies media.

Treatment for Norovirus Infection

The Norovirus genome is 7.5-8.0 kb with a 5' VPg protein cap, 3' polyadenylated tail and three open reading frames (ORFs). ORF1 encodes a nonstructural polyprotein, while ORF2 and ORF3 encode the major structural protein, VP1 and minor structural protein, VP2, respectively. The polyprotein is cleaved at five cleavage sites, yielding six proteins: p48 (NS1/2), helicase (NS3-NTPase), p22 (NS4), VPg (NS5), protease (NS6pro) and RNA-dependent RNA polymerase (NS7pol). All Norovirus proteins can be potential antiviral targets. Many viruses display high genetic heterogeneity within and between infected hosts. Assessing intrapatient viral genetic diversity is essential for designing effective vaccines, and for the success of antiviral therapy.

Disclosed herein are methods for determining whether a patient suffering from acute gastroenteritis will benefit from treatment with therapeutic agents that inhibit Norovirus genogroup II (GII), either alone or in combination with therapeutic agents that target Norovirus genogroup I (GI).

Examples of therapeutic agents that inhibit Norovirus genogroup II (GII) include GII.4/VA387-derived P particle vaccines (Kocher J et al., *J Virol.* 88(17):9728-9743 (2014)), GII.4-derived virus-like particles (VLPs) vaccines (Souza M et al., *Vaccine* 25(50):8448-8459 (2007); Debbink K et al., *J Virol.* 88(13):7256-7266 (2014)), VLPs derived from a consensus GII.4 sequence and Norwalk virus with Alhydrogel adjuvant (Parra G I et al., *Vaccine* 30(24):3580-3586 (2012)), and VLPs derived from GII.4 Human Norovirus VP1 with rotavirus VP6 antigen (Blazevic V et al., *Vaccine* 29(45):8126-8133 (2011)).

Examples of therapeutic agents that can inhibit multiple Norovirus genogroups such as Norovirus genogroup I (GI) include, but are not limited to, serum histo-blood group antigen (HBGA) blocking antibodies, ribavirin, favipiravir, 2'-C-methylcytidine, suramin-related compounds, IFNs $\alpha$, $\beta$ or $\gamma$, dipeptidyl inhibitors of norovirus 3CL protease (Kankanamalage et al., *J Med Chem.* 58(7):3144-3155 (2015); Takahashi et al., *Virus Res.* 178(2):437-444 (2013)), Pyridoxal-5'-phosphate-6-(2'-naphthylazo-6'-nitro-4',8'-disulfonate) tetrasodium salt (PPNDS), naphthalene-sulfonate inhibitors of human norovirus RNA-dependent RNA-polymerase (Tarantino et al., *Antiviral Res.* 2014; 102:23-28), naphthalene di-sulfonate (NAF2), non-nucleoside inhibitors, GI.1 plus GII.4 consensus VLP bivalent vaccine (Treanor J J et al., *J Infect Dis.* 210(11):1763-1771 (2014)), and small molecule deubiquitinase inhibitors (Gonzalez-Hernandez M J et al., *PLoS ONE* 9(4):e94491 (2014)).

In one aspect, the present disclosure provides a method for selecting a patient suffering from acute gastroenteritis for treatment with a therapeutic agent that inhibits Norovirus genogroup II (GII) comprising: (a) contacting a stool sample obtained from the patient with: (i) a first primer pair that amplifies a Norovirus genogroup I (GI) target nucleic acid comprising nucleotides that are at least 80-95% identical to SEQ ID NO: 2 or a complement thereof, and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample; (b) subjecting the reaction-sample mixture to real-time RT-PCR conditions under which each of the target nucleic acids present in the stool sample is amplified to produce a fluorescent signal; (c) detecting the fluorescent signal generated by each amplified target nucleic acid produced in step (b); and (d) selecting the patient for treatment with a therapeutic agent that inhibits Norovirus genogroup II (GII), if a fluorescent signal for the Norovirus genogroup II (GII) target nucleic acid is detected, wherein the stool sample is not subjected to an extraction or purification step prior to amplification. In some embodiments, real-time RT-PCR amplification is performed in a direct amplification disc in concert with an integrated thermal cycler.

In some embodiments, the therapeutic agent that inhibits Norovirus genogroup II (GII) is one or more agents selected from the group consisting of GII.4/VA387-derived P particle vaccines (Kocher J et al., *J Virol.* 88(17):9728-9743 (2014)), GII.4-derived virus-like particles (VLPs) vaccines (Souza M et al., *Vaccine* 25(50):8448-8459 (2007); Debbink K et al., *J Virol.* 88(13):7256-7266 (2014)), VLPs derived from a consensus GII.4 sequence and Norwalk virus with Alhydrogel adjuvant (Parra G I et al., *Vaccine* 30(24):3580-3586 (2012)), and VLPs derived from GII.4 Human Norovirus VP1 with rotavirus VP6 antigen (Blazevic V et al., *Vaccine* 29(45):8126-8133 (2011)).

In one aspect, the present disclosure provides a method for selecting a patient suffering from acute gastroenteritis for treatment with a therapeutic agent that inhibits Norovirus genogroup I (GI) comprising: (a) contacting a stool sample obtained from the patient with: (i) a first primer pair that amplifies a Norovirus genogroup I (GI) target nucleic acid comprising nucleotides that are at least 80-95% identical to SEQ ID NO: 2 or a complement thereof, and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample; (b) subjecting the reaction-sample mixture to real-time RT-PCR conditions under which each of the target nucleic acids present in the stool sample is amplified to produce a fluorescent signal; (c) detecting the fluorescent signal generated by each amplified target nucleic acid produced in step (b); and (d) selecting the patient for treatment with a therapeutic agent that inhibits Norovirus genogroup I (GI), if a fluorescent signal for the Norovirus genogroup I (GI) target nucleic acid is detected, wherein the stool sample is not subjected to an extraction or purification step prior to amplification. In some embodiments, real-time RT-PCR amplification is performed in a direct amplification disc in concert with an integrated thermal cycler.

In some embodiments of the method, the therapeutic agent that inhibits Norovirus genogroup I (GI) is one or more agents selected from the group consisting of serum histo-blood group antigen (HBGA) blocking antibodies, ribavirin, favipiravir, 2'-C-methylcytidine, suramin-related compounds, IFNs α, β or γ, dipeptidyl inhibitors of norovirus 3CL protease (Kankanamalage et al., *J Med Chem.* 58(7):3144-3155 (2015); Takahashi et al., *Virus Res.* 178(2):437-444 (2013)), Pyridoxal-5'-phosphate-6-(2'-naphthylazo-6'-nitro-4',8'-disulfonate) tetrasodium salt (PPNDS), naphthalene-sulfonate inhibitors of human norovirus RNA-dependent RNA-polymerase (Tarantino et al., *Antiviral Res.* 2014; 102:23-28), naphthalene di-sulfonate (NAF2), non-nucleoside inhibitors, GI.1 plus GII.4 consensus VLP bivalent vaccine (Treanor J J et al., *J Infect Dis.* 210(11):1763-1771 (2014)), and small molecule deubiquitinase inhibitors (Gonzalez-Hernandez M J et al., *PLoS ONE* 9(4):e94491 (2014)).

In another aspect, the present disclosure provides a method for selecting a patient suffering from acute gastroenteritis for treatment with a therapeutic agent that inhibits Norovirus genogroup II (GII) and an additional therapeutic agent that inhibits Norovirus genogroup I (GI) comprising: (a) contacting a stool sample obtained from the patient with: (i) a first primer pair that amplifies a Norovirus genogroup I (GI) target nucleic acid comprising nucleotides that are at least 80-95% identical to SEQ ID NO: 2 or a complement thereof; and (ii) a second primer pair that amplifies a Norovirus genogroup II (GII) target nucleic acid comprising nucleotides that are at least 80-95% identical to SEQ ID NO: 4 or a complement thereof, to produce a reaction-sample mixture under conditions where amplification of the Norovirus genogroup I (GI) and Norovirus genogroup II (GII) target nucleic acids, if present in the stool sample, occurs without extracting the target nucleic acids from the stool sample; (b) subjecting the reaction-sample mixture to real-time RT-PCR conditions under which each of the target nucleic acids present in the stool sample is amplified to produce a fluorescent signal; (c) detecting the fluorescent signal generated by each amplified target nucleic acid produced in step (b); and (d) selecting the patient for treatment with a therapeutic agent that inhibits Norovirus genogroup II (GII) and an additional therapeutic agent that inhibits Norovirus genogroup I (GI), if (i) a fluorescent signal for the Norovirus genogroup I (GI) target nucleic acid and a fluorescent signal for the Norovirus genogroup II (GII) target nucleic acid are detected, wherein the stool sample is not subjected to an extraction or purification step prior to amplification.

In some embodiments of the method, the additional therapeutic agent that inhibits Norovirus genogroup I (GI) is one or more agents selected from the group consisting of serum histo-blood group antigen (HBGA) blocking antibodies, ribavirin, favipiravir, 2'-C-methylcytidine, suramin-related compounds, IFNs α, β or γ, dipeptidyl inhibitors of norovirus 3CL protease (Kankanamalage et al., *J Med Chem.* 58(7):3144-3155 (2015); Takahashi et al., *Virus Res.* 178(2):437-444 (2013)), Pyridoxal-5'-phosphate-6-(2'-naphthylazo-6'-nitro-4',8'-disulfonate) tetrasodium salt (PPNDS), naphthalene-sulfonate inhibitors of human norovirus RNA-dependent RNA-polymerase (Tarantino et al., *Antiviral Res.* 2014; 102:23-28), naphthalene di-sulfonate (NAF2), non-nucleoside inhibitors, GI.1 plus GII.4 consensus VLP bivalent vaccine (Treanor J J et al., *J Infect Dis.* 210(11):1763-

1771 (2014)), and small molecule deubiquitinase inhibitors (Gonzalez-Hernandez M J et al., *PLoS ONE* 9(4):e94491 (2014)).

In some embodiments of the method, the dipeptidyl inhibitors of norovirus 3CL protease are one or more compounds selected from the group consisting of GC376, 2-Chlorobenzyl ((S)-3-cyclohexyl-1-oxo-1-(((S)-1-oxo-3-((S)-2-oxopyrrolidin-3-yl)propan-2-yl)amino)propan-2-yl) carbamate, 3-Chlorobenzyl ((S)-3-cyclohexyl-1-oxo-1-(((S)-1-oxo-3-((S)-2-oxopyrrolidin-3-yl)propan-2-yl) amino)propan-2-yl)carbamate, 3-Chlorobenzyl ((S)-1-cyclohexyl-2-oxo-2-(((S)-1-oxo-3-((S)-2-oxopyrrolidin-3-yl)propan-2-yl)amino)ethyl)carbamate, 3-Chlorobenzyl ((S)-4-methyl-1-oxo-1-(((S)-1-oxo-3-((S)-2-oxopyrrolidin-3-yl)propan-2-yl)amino)pentan-2-yl)carbamate, 4-Chlorobenzyl ((S)-3-cyclohexyl-1-oxo-1-(((S)-1-oxo-3-((S)-2-oxopyrrolidin-3-yl)propan-2-yl)amino)propan-2-yl) carbamate, 2-Fluorobenzyl ((S)-3-cyclohexyl-1-oxo-1-(((S)-1-oxo-3-((S)-2-oxopyrrolidin-3-yl)propan-2-yl) amino)propan-2-yl)carbamate, 3-Fluorobenzyl ((S)-3-cyclohexyl-1-oxo-1-(((S)-1-oxo-3-((S)-2-oxopyrrolidin-3-yl)propan-2-yl)amino)propan-2-yl)carbamate, 3-Bromobenzyl ((S)-3-cyclohexyl-1-oxo-1-(((S)-1-oxo-3-((S)-2-oxopyrrolidin-3-yl)propan-2-yl)amino)propan-2-yl) carbamate, 3-Iodobenzyl ((S)-3-cyclohexyl-1-oxo-1-(((S)-1-oxo-3-((S)-2-oxopyrrolidin-3-yl)propan-2-yl)amino) propan-2-yl)carbamate, 2-Methoxybenzyl ((S)-3-cyclohexyl-1-oxo-1-(((S)-1-oxo-3-((S)-2-oxopyrrolidin-3-yl)propan-2-yl)amino)propan-2-yl)carbamate, 3-Methoxybenzyl ((S)-3-cyclohexyl-1-oxo-1-(((S)-1-oxo-3-((S)-2-oxopyrrolidin-3-yl)propan-2-yl)amino)propan-2-yl) carbamate, 3-Cyanobenzyl ((S)-3-cyclohexyl-1-oxo-1-(((S)-1-oxo-3-((S)-2-oxopyrrolidin-3-yl)propan-2-yl) amino)propan-2-yl)carbamate, 3-((tert-Butoxycarbonyl) amino)benzyl ((S)-3-cyclohexyl-1-oxo-1-(((S)-1-oxo-3-((S)-2-oxopyrrolidin-3-yl)propan-2-yl)amino)propan-2-yl) carbamate, 3-Nitrobenzyl ((S)-3-cyclohexyl-1-oxo-1-(((S)-1-oxo-3-((S)-2-oxopyrrolidin-3-yl)propan-2-yl)amino) propan-2-yl)carbamate, Benzyl ((S)-4-methyl-1-oxo-1-(((S)-1-oxo-3-((S)-2-oxopyrrolidin-3-yl)propan-2-yl) amino)pentan-2-yl)carbamate, Benzyl ((S)-3-cyclohexyl-1-oxo-1-(((S)-1-oxo-3-((S)-2-oxopyrrolidin-3-yl)propan-2-yl) amino)propan-2-yl)carbamate, 2-Chlorobenzyl ((2S)-3-cyclohexyl-1-(((2S)-1-(diethoxyphosphoryl)-1-hydroxy-3-((S)-2-oxopyrrolidin-3-yl)propan-2-yl)amino)-1-oxopropan-2-yl)carbamate, 3-Chlorobenzyl ((2S)-3-cyclohexyl-1-(((2S)-1-(diethoxyphosphoryl)-1-hydroxy-3-((S)-2-oxopyrrolidin-3-yl)propan-2-yl)amino)-1-oxopropan-2-yl)carbamate, 2-Fluorobenzyl ((2S)-3-cyclohexyl-1-(((2S)-1-(diethoxyphosphoryl)-1-hydroxy-3-((S)-2-oxopyrrolidin-3-yl)propan-2-yl)amino)-1-oxopropan-2-yl)carbamate, 3-Bromobenzyl ((2S)-3-cyclohexyl-1-(((2S)-1-(diethoxyphosphoryl)-1-hydroxy-3-((S)-2-oxopyrrolidin-3-yl)propan-2-yl)amino)-1-oxopropan-2-yl)carbamate, Sodium (2S)-2-((S)-2-((((2-chlorobenzyl)oxy)carbonyl)amino)-3-cyclohexylpropanamido)-1-hydroxy-3-((S)-2-oxopyrrolidin-3-yl)propane-1-sulfonate, Sodium (2S)-2-((S)-2-((((3-chlorobenzyl)oxy)carbonyl)amino)-3-cyclohexylpropanamido)-1-hydroxy-3-((S)-2-oxopyrrolidin-3-yl)propane-1-sulfonate, Sodium(2S)-2-((S)-2-((((3-bromobenzyl)oxy)carbonyl)amino)-3-cyclohexylpropanamido)-1-hydroxy-3-((S)-2-oxopyrrolidin-3-yl)propane-1-sulfonate, Sodium (2S)-2-((S)-3-cyclohexyl-2-((((3-iodobenzyl)oxy)carbonyl)amino) propanemido)-1-hydroxy-3-((S)-2-oxopyrrolidin-3-yl) propane-1-sulfonate, Sodium (2S)-2-((S)-2-(((benzyloxy) carbonyl)amino)-4-methylpentanamido)-1-hydroxy-3-((S)-2-oxopyrrolidin-3-yl)propane-1-sulfonate, Sodium (2S)-2-((S)-2-(((benzyloxy)carbonyl)amino)-3-cyclohexylpropanamido)-1-hydroxy-3-((S)-2-oxopyrrolidin-3-yl)propane-1-sulfonate, 3-Chlorobenzyl ((S)-3-cyclohexyl-1-(((S)-4-(cyclopropylamino)-3,4-dioxo-1-((S)-2-oxopyrrolidin-3-yl)butan-2-yl)amino)-1-oxopropan-2-yl)carbamate, 3-Chlorobenzyl ((S)-1-(((S)-4-(cyclopropylamino)-3,4-dioxo-1-((S)-2-oxopyrrolidin-3-yl)butan-2-yl)amino)-4-methyl-1-oxopentan-2-yl)carbamate, 3-Fluorobenzyl ((S)-3-cyclohexyl-1-(((S)-4-(cyclopropylamino)-3,4-dioxo-1-((S)-2-oxopyrrolidin-3-yl)butan-2-yl) amino)-1-oxopropan-2-yl)carbamate, 3-Bromobenzyl ((S)-3-cyclohexyl-1-(((S)-4-(cyclopropylamino)-3,4-dioxo-1-((S)-2-oxopyrrolidin-3-yl)butan-2-yl)amino)-1-oxopropan-2-yl)carbamate, and Benzyl ((S)-1-(((S)-4-(cyclopropylamino)-3,4-dioxo-1-((S)-2-oxopyrrolidin-3-yl) butan-2-yl)amino)-4-methyl-1-oxopentan-2-yl)carbamate.

In some embodiments of the method, the suramin-related compounds are one or more compounds selected from the group consisting of 4-(4-Methyl-3-nitrobenzamido)naphthalene-1,5-disulphonate acid disodium salt, 4-(3-Amino-4-methylbenzamido)naphthalene-1,5-disulphonate acid disodium salt, 4-[4-Methyl-3-(3-nitrobenzamido)benzamido] naphthalene-1,5-disulsulphonate acid disodium salt, 4-[3-(3-Aminobenzamido)-4-methylbenzamido]naphthalene-1, 5-disulphonate acid disodium salt, and 4-4'-(Carbonylbis [imino-3,1-phenylenecarbonylimino(4-methyl-3,1-phenylene) carbonylimino])bis-1,5-naphthalenedisulphonate acid tetrasodium salt.

In certain embodiments of the method, the nonnucleoside inhibitors are selected from the group consisting of NIC02, NIC04, NIC10 and NIC 12 (See Eltahla et al., *Antimicrob Agents Chemother.* 58(6):3115-3123 (2014)).

In some embodiments of the method, wherein the therapeutic agent that inhibits Norovirus genogroup II (GII) is one or more agents selected from the group consisting of GII.4/VA387-derived P particle vaccines (Kocher J et al., *J Virol.* 88(17):9728-9743 (2014)), GII.4-derived virus-like particles (VLPs) vaccines (Souza M et al., *Vaccine* 25(50): 8448-8459 (2007); Debbink K et al., *J Virol.* 88(13):7256-7266 (2014)), VLPs derived from a consensus GII.4 sequence and Norwalk virus with Alhydrogel adjuvant (Parra G I et al., *Vaccine* 30(24):3580-3586 (2012)), and VLPs derived from GII.4 Human Norovirus VP1 with rotavirus VP6 antigen (Blazevic V et al., *Vaccine* 29(45): 8126-8133 (2011)).

Kits

The present disclosure also provides kits for detecting target nucleic acid sequences corresponding to pathogenic Norovirus genogroups (e.g., GI and GII). In some embodiments, Norovirus genogroup I (GI) comprises a genotype selected from the group consisting of GI.1, GI.2, GI.3, GI.4, GI.5, GI.6, GI.7, GI.8, GI.9, GI.10 and GI.14. In certain embodiments, Norovirus genogroup II (GII) comprises a genotype selected from the group consisting of GII.1, GII.2, GII.3, GII.4, GII.5, GII.6, GII.7, GII.8, GII.9, GII.10, GII.11, GII.12, GII.13, GII.14, GII.15, GII.16, GII.17, GII.18, GII.19, GII.20, GII.21, GII.22, and GII.23.

Kits of the present technology comprise at least two oligonucleotides which may serve as primers or primer-probes for amplifying one or more target nucleic acid sequences corresponding to a Norovirus genogroup (e.g., GI and GII) to determine the presence of pathogenic Norovirus genogroups (e.g., GI and GII) in a biological sample.

In some embodiments, the kits of the present technology comprise a single primer pair that specifically hybridizes to a target nucleic acid corresponding to a Norovirus genogroup selected from the group consisting of GI and GII. In other embodiments, the kits of the present technology comprise multiple primer pairs comprising a first primer pair that specifically hybridizes to a target nucleic acid corresponding to Norovirus genogroup I (GI), and a second primer pair that specifically hybridizes to a target nucleic acid corresponding to Norovirus genogroup II (GII).

In any of the above embodiments, the target nucleic acid corresponding to Norovirus genogroup I (GI) comprises a nucleotide sequence that is at least 80-95% identical to SEQ ID NO: 2 or a complement thereof, and the target nucleic acid corresponding to Norovirus genogroup II (GII) comprises a nucleotide sequence that is at least 80-95% identical to SEQ ID NO: 4 or a complement thereof.

In some embodiments, the kits comprise a first primer pair that is capable of specifically hybridizing to a target nucleic acid corresponding to Norovirus genogroup I (GI) comprising nucleotides that are at least 80-95% identical to SEQ ID NO: 2, or a complement thereof. Additionally or alternatively, the kits comprise a second primer pair that is capable of specifically hybridizing to a target nucleic acid corresponding to Norovirus genogroup II (GII) comprising nucleotides that are at least 80-95% identical to SEQ ID NO: 4, or a complement thereof.

In some embodiments, the kits comprise one or more primer pairs selected from among 5'd CGYTGGATGCGIT-TYCATGA 3' (SEQ ID NO: 5), and 5'd TCCTTAGACGC-CATCATCATTTAC 3' (SEQ ID NO: 6) (GI primer pair); and 5'd TGTTYAGGTGGATGAGRTTCTCIGA 3' (SEQ ID NO: 9) and 5'd TCGACGCCATCTTCATTCACA 3' (SEQ ID NO: 10) (GII primer pair). Additionally or alternatively, the kits comprise an internal control primer pair consisting of a third forward primer comprising 5'd CTCGTCGACAATGGCGGAA 3' (SEQ ID NO: 13) and a third reverse primer comprising 5'd TTCAGCGACCCCGT-TAGC 3' (SEQ ID NO: 14).

Additionally or alternatively, in some embodiments, the kits provide a single nucleic acid probe that specifically hybridizes to a target nucleic acid corresponding to a Norovirus genogroup selected from the group consisting of GI and GII. In other embodiments, the kits of the present technology comprise multiple nucleic acid probes comprising at least one nucleic acid probe that specifically hybridizes to a target nucleic acid corresponding to Norovirus genogroup I (GI) comprising nucleotides that are at least 80-95% identical to SEQ ID NO: 2, or a complement thereof and/or at least one nucleic acid probe that specifically hybridizes to a target nucleic acid corresponding to Norovirus genogroup II (GII) comprising nucleotides that are at least 80-95% identical to SEQ ID NO: 4, or a complement thereof.

In some embodiments, the kit comprises a first nucleic acid probe that specifically hybridizes to a segment of a target nucleic acid corresponding to Norovirus genogroup I (GI) comprising nucleotides that are at least 80-95% identical to SEQ ID NO: 2, or a complement thereof, and is detectably labeled with a fluorophore.

Additionally or alternatively, in some embodiments, the kit comprises a second nucleic acid probe that specifically hybridizes to a segment of a target nucleic acid corresponding to Norovirus genogroup I (GI) comprising nucleotides that are at least 80-95% identical to SEQ ID NO: 2, or a complement thereof, and is detectably labeled with a fluorophore. In certain embodiments, the kit further comprises a third nucleic acid probe that specifically hybridizes to a segment of a target nucleic acid corresponding to Norovirus genogroup II (GII) comprising nucleotides that are at least 80-95% identical to SEQ ID NO: 4, or a complement thereof, and is detectably labeled with a fluorophore.

In some embodiments, the kits comprise one or more nucleic acid probes selected from among 5'd TGGACAG-GAGAYCGCIATCTCYTGCCCGA 3' (SEQ ID NO: 7) or a complement thereof (GI probe); 5'd TGGACAG-GAGATCGCAATCTACTGCCTGA 3' (SEQ ID NO: 8) or a complement thereof (GI probe); and 5'd ACGTGG-GAGGGCGATCGCAATCT 3' (SEQ ID NO: 11) or a complement thereof (GII probe). Additionally or alternatively, the kits comprise an internal control nucleic acid probe comprising the sequence 5'd GCTTGGGGCGACAGTCACGTCGC 3' (SEQ ID NO: 15) or a complement thereof.

In some embodiments, the kit comprises liquid medium containing the at least one target-specific nucleic acid probe in a concentration of 750 nM or less. With such a kit, the probes are provided in the required amount to perform reliable multiplex detection reactions according to the present technology. In some embodiments, the target-specific nucleic acid probes are detectably labeled.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of target nucleic acid sequences corresponding to Norovirus genogroups (e.g., GI and GII).

In one embodiment, the kits of the present technology further comprise a positive control nucleic acid sequence and a negative control nucleic acid sequence to ensure the integrity of the assay during experimental runs. A kit may further contain a means for comparing the copy number of one or more of Norovirus genogroup I (GI) and Norovirus genogroup II (GII) in a stool sample with a reference nucleic acid sample (e.g., a sample having a known copy number for one or more of Norovirus genogroup I (GI) and Norovirus genogroup II (GII)). The kit may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kit additionally may comprise an assay definition scan card and/or instructions such as printed or electronic instructions for using the oligonucleotides in an assay. In some embodiments, a kit comprises an amplification reaction mixture or an amplification master mix. Reagents included in the kit may be contained in one or more containers, such as a vial.

Primers, probes, and/or primer-probes specific for amplification and detection of DNA internal control may be included in the amplification master mix as the target primer pairs to monitor potential PCR inhibition. Reagents necessary for amplification and detection of targets and internal control may be formulated as an all-in-one amplification master mix, which may be provided as single reaction aliquots in a kit.

EXAMPLES

Example 1: Detection of Norovirus Genogroups Using SIMPLEXA™ Direct Real-Time RT-PCR Real-time RT-PCR Amplification and Detection: Raw formed and unformed stool specimens were suspended in sample buffer. For each reaction on the Direct Amplification Disc (Focus Diagnostics, Inc., Cypress, Calif, USA), 50 µL or mg of each unprocessed stool sample was suspended in 2 mL of sample buffer (or similar proportions, i.e., 25 µL or mg into 1 mL of sample buffer). Next, 50 µL of each stool-sample buffer mixture was loaded into the sample port without performing a separate front-end specimen preparation step. 50 µL of Norovirus Direct Reaction Mix was loaded into the reaction port, wherein the reaction mix consisted of PCR buffer, DNA polymerase, reverse transcriptase, RNase inhibitor, BSA, dNTPs, magnesium chloride, potassium chloride, primers consisting of SEQ ID NOs: 5, 6, 9 and 10 (each primer having a concentration of 750 nM), probes consisting of SEQ ID NOs: 7, 8 and 11 (each probe having a concentration of 750 nM), and an internal control Enterobacteria MS2 phage RNA and a primer pair and probe specific to the control MS2 phage (SEQ ID NOs: 13-15) (each control primer and control probe having a concentration of 187.5 nM). The concentration in the reaction well when the reaction mix and sample were combined was 600 nM for each of the GI and GII primers and probes, and 150 nM for each of the control primers and probe (or 80% of the above starting values, respectively).

The probes consisting of SEQ ID NOs: 7, 8, 11 and 15 were labeled with CFR610, CFR610, FAM and Q670 respectively. All testing was performed using the Integrated Cycler instrument (Focus Diagnostics, Cypress, CA). The PCR cycling conditions include the following steps:

| Step | Temp (° C.) | Time | Cycles |
|---|---|---|---|
| | open laser valve from sample port | | |
| 1 | 97 | 10 min | 1 |
| 2 | 60 | 1 sec | 1 |
| | open laser valve from reaction mix port | | |
| 3 | 50 | 2 min* | 1 |
| 4 | 50 | 13 min | |
| 5 | 97 | 2 min | 1 |
| 6 | 97 | 10 sec | 42 |
| | 56 | 30 sec*** | |

| Target | Channel | Threshold | Cycle Cut-Off |
|---|---|---|---|
| Norovirus GI | CFR610 | 5,000 | 42 |
| Norovirus GII | FAM | 5,000 | 42 |
| Internal Control | Q670 | 5,000 | 42 |

Data collection and analysis were performed with Integrated Cycler Studio software. A positive control spiked with Norovirus and a negative control were included in the assay. Results were generated in approximately 90 minutes.

Limit of Detection (LoD): Limit of detection (LoD) studies were performed to determine analytical sensitivity. Norovirus genotypes GI.1 and GII.4 (ZeptoMetrix, Buffalo, NY) were used in the Limit of detection (LoD) study. The LoD for each viral stock refers to the lowest concentration at which ≥95% detection of Norovirus was observed in pooled human formed negative stool matrix (pooled from 10 clinical specimens) or in pooled human unformed negative stool matrix (pooled from 10 clinical specimens).

Analytical Reactivity: A panel of 20 de-identified clinical stool specimens (Focus Diagnostics: Reference Laboratory), previously tested using real-time RT-PCR, were genotyped via sequencing. The 20 specimens represented 5 different genotypes from GI (GI.2, GI.3, GI.6, GI.7, and GI.8) and 9 different genotypes from GII (GII.2, GII.3, GII.4, GII.5, GII.6, GII.7, GII.10, GII.13 and GII.14). All 20 specimens were evaluated using the SIMPLEXA™ Norovirus Direct assay. Control specimens purchased from external vendors were also assessed.

TABLE 1

LoD for GI.1 and GII.4 Genotypes in Formed Stool

| Genogroup (Genotype) | LOD (TCID$_{50}$/mL) | Mean Ct | Min. Ct | Max. Ct | Replicates Detected |
|---|---|---|---|---|---|
| GI (GI.1) | $4.10 \times 10^4$ | 35.8 | 32.1 | 37.3 | 20/20 (100%) |
| GII (GII.4) | $1.23 \times 10^4$ | 39.0 | 37.4 | 40.5 | 20/20 (100%) |

TABLE 2

LoD for GI.1 and GII.4 Genotypes in Unformed Stool

| Genogroup (Genotype) | LOD (TCID$_{50}$/mL) | Mean Ct | Min. Ct | Max. Ct | Replicates Detected |
|---|---|---|---|---|---|
| GI (GI.1) | $4.10 \times 10^4$ | 36.3 | 35.6 | 37.5 | 24/24 (100%) |
| GII (GII.4) | $6.15 \times 10^3$ | 38.7 | 32.5 | 43.5 | 20/20 (100%) |

Results. LoD studies showed that the SIMPLEXA™ Norovirus Direct assay detected Norovirus GI (GI.1 genotype) at $4.10 \times 10^4$ TCID$_{50}$/mL and Norovirus GII (GII.4 genotype) at $1.23 \times 10^4$ TCID$_{50}$/mL in formed stool (Table 1). Norovirus GI (GI.1 genotype) LoD and Norovirus GII (GII.4 genotype) LoD were $4.10 \times 10^4$ and $6.15 \times 10^3$ TCID$_{50}$/mL in unformed stool, respectively (Table 2). The SIMIPLEXA™ Norovirus Direct assay was able to detect genotypes GI.2, GI.3, GI.6, GI.7, and GI.8 from the GI genogroup. Genotype GI.1 was already tested in the LoD study. The assay also detected genotypes GII.2, GII.3, GII.4 (Sydney), GII.5, GII.6, GII.7, GII.10, GII.13, and GII.14 from the GII genogroup. All other genotypes were not available for evaluation.

These results demonstrate that the SIMPLEXA™ Norovirus Direct assay was capable of directly detecting and differentiating between Norovirus GI and GII genogroups in raw formed and unformed stool specimens without requiring a separate nucleic acid extraction step.

Example 2: Comparison of Norovirus SIMPLEXA™ Direct Real-Time RT-PCR Results to Conventional Real-Time RT-PCR 144 de-identified clinical stool specimens (47 GI positive, 43 GII-positive, and 54 norovirus-negative from Focus Diagnostics: Reference Laboratory) that were previously tested using conventional real-time RT-PCR, were evaluated for Norovirus using the SIMPLEXA™ Norovirus Direct assay. The results of the SIMPLEXA™ Norovirus Direct assay were compared with the previous real-time RT-PCR results to determine positive and negative agreements. Conventional real-time RT-PCR employs a separate nucleic acid extraction step prior to performing the amplification step of real-time RT-PCR.

TABLE 3

Norovirus GI Concordance for Stool Specimens

| Simplexa ™ | Previous Results | | | |
|---|---|---|---|---|
| | GI Positive | GI Negative | Total | GI % Agreement |
| GI Positive | 42 | 0 | 42 | Positive Agreement 89.4% (42/47) |
| GI Negative | 5[a] | 97 | 102 | Negative Agreement 100% (97/97) |
| Total | 47 | 97 | 144 | |

[a]The 5 specimens were previously tested using conventional real-time RT-PCR and were subsequently tested using the SIMPLEXA ™ Norovirus Direct assay. Using CDC Norovirus Taqman Assay in combination with Roche's MagNa Pure extraction system, 4 of the 5 specimens tested negative on the CDC assay.

TABLE 4

Norovirus GII Concordance for Stool Specimens

| Simplexa ™ | Previous Results | | | |
|---|---|---|---|---|
| | GI Positive | GI Negative | Total | GI % Agreement |
| GI Positive | 43 | 0 | 43 | Positive Agreement 100% (43/43) |
| GI Negative | 0 | 101 | 101 | Negative Agreement 100% (101/101) |
| Total | 43 | 101 | 144 | |

Results. Using the 144 de-identified clinical specimens, the percent positive and negative agreements with conventional real-time RT-PCR results for Norovirus GI were >89% (42/47) and 100% (97/97) for clinical stool specimens (Table 3), respectively. The percent positive and negative agreements with conventional real-time RT-PCR results for Norovirus GII were 100% (43/43) and 100% (101/101) for clinical stool specimens (Table 4), respectively. These results demonstrate that the SIMPLEXA™ Norovirus Direct assay was capable of directly detecting and differentiating between Norovirus GI and GII genogroups in raw formed and unformed stool specimens without requiring a separate nucleic acid extraction step, and had a performance that was comparable to that observed with conventional real-time RT-PCR, which employed nucleic acid extraction.

Example 3: Impact of Endogenous and Exogenous Interferents on the Sensitivity of the Norovirus Multiplex Assay The effect of potential endogenous and exogenous interfering substances on the sensitivity of the Norovirus multiplex assay was assessed.

The interference panel was contrived with GI.1 or GII.4 at 3 times the LoD concentration. Each substance was spiked into Norovirus GI.1 or GII.4 contrived samples and was tested using SIMPLEXA™ Norovirus Direct. The concentration of each interferent is listed in Tables 5-6. Pooled formed negative stool matrix or pooled unformed negative stool matrix was used in creating the panel.

TABLE 5

Exogenous Interferents Tested in Human Stool Matrix

| Potential Interferent | Tested Concentration of Interferent | Tested Concentration of Norovirus |
|---|---|---|
| Acetaminophen | 5% (w/v) | Formed Stool Matrix |
| Amoxicillin | 5% (w/v) | GI.1: $1.23 \times 10^5$ TCID$_{50}$/mL (3× LoD) |
| Ampicillin | 152 µmol/L | GII.4: $3.69 \times 10^4$ TCID$_{50}$/mL (3× LoD) |
| Ibuprofen | 5% (w/v) | Unformed Stool Matrix |
| Metronidazole | 5% (w/v) | GI.1: $1.23 \times 10^5$ TCID$_{50}$/mL (3× LoD) |
| Naprosyn | 2.2 µmol/L | GII.4: $1.85 \times 10^4$ TCID$_{50}$/mL (3× LoD) |
| Antiseptic Towelettes | 1% (w/v) | |
| Pepto-Bismol | 1% (w/v) | |
| Aspartame | 5% (w/v) | |
| Barium Sulfate | 5% (w/v) | |
| CaCO$_3$ | 5% (w/v) | |
| Nystatin | 10,000 USP Units/mL | |
| Senna glycosides (Sennosides) | 5% (w/v) | |
| 1% Hydrocortisone Cream | 50% (w/v) | |
| Imodium | 5% (w/v) | |
| Mg(OH)$_2$, Al(OH)$_3$ and MgCO$_3$ | 5% (w/v) | |
| Polymyxin B Sulfate Bacitrin Zinc | 50% (w/v) | |
| Rexall Mineral Oil Laxative | 50% (w/v) | |

TABLE 6

Endogenous Interferents Tested in Human Stool Matrix

| Potential Interferent | Tested Concentration of Interferent | Tested Concentration of Norovirus |
|---|---|---|
| Cholesterol | 5% (w/v) | See Table 5 |
| Hemoglobin | 12.5% (w/v) | |
| Steric Acid/Palmitic Acid (1:1) | 5% (w/w) | |
| Mucin | 5% (w/w) | |
| Triglyceride | 5% (w/w) | |
| Whole Blood | 10% (w/w) | |

Results. No interference was detected with any of the tested exogenous interferents (listed in Table 5) and endogenous interferents (listed in Table 6) in both formed and unformed stool matrices.

Example 4: Cross-Reactivity of the Norovirus Multiplex Assay

Cross-reactivity studies were conducted using a diverse panel of bacteria, fungi, parasites, and viruses. About $10^6$ CFU/mL of bacteria, $10^6$ CFU/mL of fungi, $10^6$ cells/mL of parasites, or 105 TCID$_{50}$/mL of viruses were diluted into negative formed and unformed human stool matrices, and the Norovirus multiplex assay was performed on each test sample. Table 7 provides a complete list of the different pathogens that were tested. The cut-off Ct value for positive cross-reactivity was 42 cycles.

TABLE 7

Cross-reactivity Pathogens Tested in Raw Formed and Unformed Stool Matrices

| | | |
|---|---|---|
| Acinetobacter baumannii | Escherichia coli (O145:H48) | Serratia liquefaciens |
| Acinetobacter lwoffii | Escherichia hermannii | Serratia marcescens |
| Aeromonas caviae complex | Fusobacterium necrophorum | Shigella sonnei |
| Aeromonas hydrophila | Helicobacter pylori | Staphylococcus aureus |
| Bacteroides fragilis | Klebsiella pneumoniae | Staphylococcus epidermidis |
| Campylobacter coli | Lactococcus lactis | Streptococcus agalactiae |
| Campylobacter jejuni | Listeria monocytogenes | Streptococcus dysgalactiae |
| Citrobacter freundii | Micrococcus luteus | Streptococcus pyogenes |
| Clostridium difficile | Morganella morganii | Vibrio cholerae |
| Eggerthella lenta | Peptostreptococcus anaerobius | Vibrio parahaemolyticus |
| Enterobacter cloacae | Plesiomonas shigelloides | Candida albicans |
| Enterococcus casseliflavus | Proteus mirabilis | Cryptosporidium parvum |
| Enterococcus faecalis | Proteus vulgaris | Entamoeba histolytica |
| Enterococcus faecium | Providencia alcalifaciens | Giardia lamblia |
| Enterococcus gallinarum | Providencia stuartii | Adenovirus 1 |
| Escherichia coli (O157:H7) | Pseudomonas aeruginosa | Adenovirus 7A |
| Escherichia coli (O26:H4) | Pseudomonas fluorescens | Adenovirus Type 40 |
| Escherichia coli (O45:H2) | Pseudomonas putida | Coxsackievirus A16 |
| Escherichia coli (O103:H11) | Salmonella agona | Echovirus 9 |
| Escherichia coli (O111:NM) | Salmonella bongori | Parechovirus Type 3 |
| Escherichia coli (O121:H19) | Salmonella enterica | Rotavirus Strain Wa |

Results. No cross-reactivity was detected with any of the pathogens listed in Table 7.

The above Examples demonstrate that the Norovirus multiplex assay of the present technology is capable of rapidly detecting and discriminating between Norovirus GI and GII genogroups in both formed and unformed stool specimens, and does not require the extraction of viral nucleic acids from the stool specimen prior to performing real-time RT-PCR.

Example 5: Detection of Norovirus from a Simulated Rectal Swab in Liquid Amies Transport Media This Example evaluates the ability of the Norovirus multiplex assay of the present technology to detect norovirus when using a simulated rectal swab in liquid Amies as the sample input.

Clarified Norovirus GII.4 Sydney at different viral loads was used to prepare contrived stool samples in liquid Amies media. In Preparation A, 25 mg of pooled stool matrix was added to 1 mL Amies media. A total of 4 samples were prepared. Clarified GII virus was spiked into the 4 samples to generate a 1000×, 100×, 10× and 1× viral load samples. Preparation B was prepared the same way except the amount of stool was increased to 50 mg and the viral load was doubled to reflect the increase in the amount of stool used. The results are provided below:

| Viral Load | 25 mg stool | | 50 mg stool | |
|---|---|---|---|---|
| | Noro | IC | Noro | IC |
| 1000X | 27.3 | 36.1 | 27.3 | 31.0 |
| | 27.3 | 36.8 | 27.6 | 31.9 |
| 100X | 31.7 | 38.3 | 30.7 | 31.0 |
| | 32.7 | 0* | 30.9 | 31.8 |
| 10X | 35.8 | 35.9 | 34.2 | 30.6 |
| | 35.2 | 34.8 | 33.7 | 31.1 |
| 1X | 40.2 | 34 | 39.6 | 32.3 |
| | 41.3 | 35 | 38.7 | 31.4 |

*Internal control signal not required for valid result when target is positive.

Across all viral loads, Norovirus GII.4 was detected in the simulated rectal swab contrived stool samples in liquid Amies run directly without dilution in the Norovirus multiplex assay of the present technology.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A kit for detecting the presence of Norovirus genogroup I (GI) in a biological sample comprising a first primer pair that amplifies a Norovirus genogroup I (GI) target nucleic acid of SEQ ID NO: 2 or a complement thereof, wherein the first primer pair consists of a first forward primer comprising 5'd CGYTGGATGCGITTYCATGA 3' (SEQ ID NO: 5) and a first reverse primer comprising 5'd TCCTTAGACGCCATCATCATTTAC 3'(SEQ ID NO: 6).

2. The kit of claim 1, further comprising a second primer pair that amplifies a control target nucleic acid of SEQ ID NO: 12 or a complement thereof.

3. The kit of claim 2, wherein the second primer pair consists of a second forward primer comprising 5'd CTCGTCGACAATGGCGGAA 3' (SEQ ID NO: 13) and a second reverse primer comprising 5'd TTCAGCGACCCCGTTAGC 3' (SEQ ID NO: 14).

4. The kit of claim 1, wherein the kit further comprises:
a first nucleic acid probe that is capable of specifically hybridizing to a segment of the Norovirus genogroup I (GI) target nucleic acid sequence of SEQ ID NO: 2 or a complement thereof, wherein the first nucleic acid probe is detectably labeled and optionally comprises 5'd TGGACAGGAGAYCGCIATCTCYTGCCCGA 3' (SEQ ID NO: 7), or a complement thereof; and/or
a second nucleic acid probe that is capable of specifically hybridizing to a segment of the Norovirus genogroup I (GI) target nucleic acid sequence of SEQ ID NO: 2 or a complement thereof, wherein the second nucleic acid probe is detectably labeled and optionally comprises 5'd TGGACAGGAGATCGCAATCTACTGCCTGA 3'(SEQ ID NO: 8), or a complement thereof; and/or
a third nucleic acid probe that specifically hybridizes to a segment of the control target nucleic acid of SEQ ID NO: 12 or a complement thereof, wherein the third nucleic acid probe is detectably labeled and comprises 5'd GCTTGGGGCGACAGTCACGTCGC 3' (SEQ ID NO: 15), or a complement thereof.

5. The kit of claim 4, wherein the first nucleic acid probe is detectably labelled with CFR610 fluorophore.

6. The kit of claim 4, wherein the second nucleic acid probe is detectably labelled with CFR610 fluorophore.

7. The kit of claim 4, wherein the third nucleic acid probe is detectably labelled with Q670 fluorophore.

8. A kit for detecting the presence of Norovirus genogroup II (GII) in a biological sample comprising a primer pair that amplifies a Norovirus genogroup II (GII) target nucleic acid of SEQ ID NO: 4 or a complement thereof, wherein the primer pair consists of a second forward primer comprising 5'd TGTTYAGGTGGATGAGRTTCTCIGA 3' (SEQ ID NO: 9) and a second reverse primer comprising 5'd TCGACGCCATCTTCATTCACA 3' (SEQ ID NO: 10).

9. The kit of claim 8, further comprising a control primer pair that amplifies a control target nucleic acid of SEQ ID NO: 12 or a complement thereof.

10. The kit of claim 9, wherein the control primer pair consists of a second forward primer comprising 5'd CTCGTCGACAATGGCGGAA 3' (SEQ ID NO: 13) and a second reverse primer comprising 5'd TTCAGCGACCCCGTTAGC 3' (SEQ ID NO: 14).

11. The kit of claim 8, wherein the kit further comprises:
a nucleic acid probe that is capable of specifically hybridizing to a segment of the Norovirus genogroup II (GII) target nucleic acid sequence of SEQ ID NO: 4 or a complement thereof, wherein the third nucleic acid probe is detectably labeled and optionally comprises 5'd ACGTGGGAGGGCGATCGCAATCT 3' (SEQ ID NO: 11) or a complement thereof; and/or
a control nucleic acid probe that specifically hybridizes to a segment of the control target nucleic acid of SEQ ID NO: 12 or a complement thereof, wherein the fourth nucleic acid probe is detectably labeled and comprises 5'd GCTTGGGGCGACAGTCACGTCGC 3' (SEQ ID NO: 15), or a complement thereof.

12. The kit of claim 11, wherein the nucleic acid probe is detectably labelled with FAM fluorophore.

13. The kit of claim 11, wherein the control nucleic acid probe is detectably labelled with CFR610 fluorophore.

* * * * *

```
                            SEQUENCE LISTING

Sequence total quantity: 15
SEQ ID NO: 1            moltype = DNA   length = 7699
FEATURE                 Location/Qualifiers
source                  1..7699
                        mol_type = unassigned DNA
                        organism = unidentified
                        note = Norovirus Hu/GI.2/Leuven/2003/BEL
SEQUENCE: 1
gtgaatgatg atggcgtcga aagacgtcgt tgcaactaat gttgcaagca acaacaatgc    60
taacaacact agtgctacat ctcgattttt atcgagattt aagggcttag gaggtggcgc   120
aagcccccct agtcctataa aaattaaaag tacagaaatg gctctgggat taattggcag   180
aacaactcca gaaccaacag ggaccgctgg tccaccgccc aaacaacaga gggaccgacc   240
tcccagaact caggaggagg tccagtatgg tatgggatgg tctgacaggc ccattgatca   300
aaacgttaaa tcatgggaag agcttgatac cacagtcagg gaagagatct tagacaacca   360
caaagagtgg tttgacgctg gtggtttggg tccttgcaca atgcctccaa catatgaacg   420
ggtcagggat gacagtccac ctggtgaaca ggttaaatgg tccgcgcgtg atggagtcaa   480
cattggagtg gagcgcctca caacagtgag tggacccgag tggaaccttt gccctctacc   540
ccccattgac ttaaggaaca tggagccagc cagtgaaccn actattggag atatgataga   600
attctatgaa ggccacatct atcattactc catatacatt gggcaaggca aaacagtcgg   660
tgtccattct ccacaggcag cgttctcagt ggctagggtg accatccagc ccatagccgc   720
ttggtggaga gtttgttaca tacccaacc caagcacaga ctgagttacg accaactcaa   780
ggaattagag aatgagccat ggccatatgc ggccataact aataattgtt ttgaattctg   840
ctgtcaagtc atgaaccttg aggacacgtg gttacagagg cggttgatca cgtcgggtag   900
attccaccac cccaccaat cgtggtcaca gcagacccct gagttccagc aagatagcaa   960
gttagagttg gtcagggatg ctatattagc tgcagtgaat ggtcttgttt cgcagccctt  1020
caagaatttc ttgggtaaac tcaaacctct caatgtgctc aacattttgt ctaattgtga  1080
ttggaccttc atgggagtgg tggagatggt tatactatta cttgaactct ttggcgtgtt  1140
ctggaacccg cctgatgtgt ccaattttat agcgtccctt ctccctgatt tccatcttca  1200
aggacctgaa gacttggcac gagatctagt cccagtgatt cttggcggca taggattggc  1260
catcgggttc accagagaca aagttacaaa ggttatgaag agtgctgtgg atggtcttcg  1320
agctgctaca caactgggac aatatgggtt tcactactca agaagtattt  1380
ctttggggg gaccagactg agcgcaccct caaaggcatt gaggcggcag tcatagatat  1440
ggaagtgttg tcctccacat cagtgacaca gctagtgaga gacaaacagg cagcaaaagc  1500
ttatatgaac atcttggaca atgaagaaga gaaagccagg aagctctcag ctaaaaacgc  1560
tgacccacat gtgatatcct caacaaatgc cctaatatcg cgtatttcca tggcacgatc  1620
tgcattggcc aaggcccagg ctgagatgac cagtcgaatg agaccagttg ttattatgat  1680
gtgtggcccg cctgggattg ggaagaccaa ggctgctgag cacctagcta agcgtctagc  1740
taatgagatc agacctggtg gtaaggtggg gttggttccc cgtgaagctg tcgaccactg  1800
ggacggttat catggtgagg aagtgatgct gtgggacgac tatgccatga caaaaataca  1860
agatgactgt aataaactcc aagccattgc tgattcggcc ccactcacct taaattgtga  1920
caggattgaa aacaaaggaa tgcagttcgt ttcagatgca atagtcatca ctaccaacgc  1980
cccaggcccc gccctgtgg actttgtcaa ccttggacca gtgtgtagac gggtcgactt  2040
cttggtctac tgctctgccc cagaggtgga acagatacgg agggtcgccc ctggtgatac  2100
atcagcactg aaagactgtt ttaagccaga cttctctcat ttaaaaatgg agctggctcc  2160
acaaggtggg tttgacaatc aagggaacac accgtttggc aaaggcacca tgaagccaac  2220
aaccattaac agacttctca tacaagctgt ggcccttacc atgaaaggc aggatgagtt  2280
tcagttacag gggaagatgt atgactttga tgatgacagg gtgtcagcat tcaccaccat  2340
ggcacgtgat aatggcctgg gcatcttgag catggcaggt ctgggcaaga agctacgtgg  2400
tgttacaacg atggagggct taaagaatgc cctaaagggg tacaaaatca atgcgtgcac  2460
aataaaatgg caggccaaag tgtactcact agaatcagat ggcaacagtg tcaacattaa  2520
agaggagagg aacgtcttaa ctcagcaaca acagtcggtg tgtgccgcct ctgtcgcgct  2580
cactcgtctt cgggctgcgc gcgcggtggc atacgcatcg tgcatccaat cggctacaac  2640
ttctatacta caaattgctg gctcagcct agtggtcaac agagcagtga agagaatgtt  2700
tggcacgcgc acagccacct tgtccctaga gggccccccc agagaacaca aatgcagggt  2760
ccacatggcc aaggccgcag gaaagggacc tattggccat gatgatgtgg tagaaaagta  2820
tgggcttttgc gaaacagagg aggacgaaga agtgccccac gctgaaatcc cttctgctac  2880
catggagggc aagaacaaag ggaagaacaa gaaaggacgt ggtcggagga caattacaa  2940
cgccttctcc cgcagaggac tcaatgatga agagtacgaa gagtacaaga gatacgcga  3000
ggagaaaggt ggcaactaca gcatacagga gtacctagaa gacagacaaa ggtatgaaga  3060
agagctggca gaggttcaag caggtggaga tggaggaatt ggggaaactg aaatggaaat  3120
ccgccacaga gtgttctaca aatccaagag cagaaagcat catcaggaag aacgacgcca  3180
gctagggctg gtgacaggtt ccgacattcg gaagagaaaa ccaatcgact ggacccccac  3240
caagtcagca tgggcagatg atgagcgtga ggtggattac aatgagaaga tcagcttcga  3300
ggcgccccc acttttatgga gtagagtgac aaagtttggg tctggatggg gtttctgggt  3360
cagccctaca gtcttcataa ccacaacgca cgttatacca accagtgcaa aggagttctt  3420
tggtgaaccc ctaaccagca tagctatcca cagggctggt gagttcactc tcttcaggtt  3480
```

```
ttcaaagaaa attaggcctg atctcacagg tatgatcctt gaggagggtt gccccgaggg    3540
cacggtgtgt tcagtactaa taaaaaggga ctctggtgaa ctactgccat tggccgtgag    3600
gatgggcgca atagcatcaa tgcgcataca gggccgcctt gtccatgggc aatctggcat    3660
gttactcacc ggggcaaatg ctaagggcat ggaccttgga accatcccag gggattgtgg    3720
ggctccttat gtttataaga gggctaatga ctgggtggtc tgtggtgtac atgccgctgc    3780
caccaagtca ggcaacaccg ttgtgtgcgc cgttcaggcc agtgaaggag aaactacgct    3840
tgaaggcggt gacaaaggtc attatgctgg acatgaaata attaagcatg gttgtggacc    3900
agctctatca accaaaacca aattctggaa atcatccccc gaaccactgc ccctggggt    3960
ctacgagccc gcctacctcg ggggccggga ccctagggtg tctggcggtc cctcactcca    4020
acaagtgttg cgggatcagt taaagccatt tgctgagcca cgaggacgta tgccagaacc    4080
aggtctcttg gaggccgcag ttgagactgt gacttcatca ttagagcagg ttatggacac    4140
tcccgttcct tggagctata gtgatgcgtg ccagtcccct gacaagacca ctagttctgg    4200
tttcccctac catagaagga agaatgacga ctgaatggc accaccttg ttagggagtt    4260
aggggagcag gcggcacacg ctaataacat gtatgagcag gctaaagta tgaaacccat    4320
gtacacggca gcacttaaag atgaactagt caaaccagag aaagtatacc agaaagtgaa    4380
aaagcgcttg ttatggggag cagacttggg cacggtagtt cgggccgcac gggcttttgg    4440
cccattctgt gatgctataa aatcccacac aatcaaattg cctatcaaag ttggaatgaa    4500
ttcaattgag gatggaccac tgatctatgc agaacattcg aaatataagt accattttga    4560
tgcagattac acagcttggg attcaactca aaataggcaa atcatgacag agtcattttc    4620
aatcatgtgt cggctaactg catcacctga attagcttca gtggtggctc aagacttgct    4680
cgcaccttca gagatggatg ttggtgacta cgtcataaga gtgaaggaag gtctcccatc    4740
tggtttccca tgcacatcac aagttaatag cataaaccat tggttaataa ctctgtgtgc    4800
cctttctgaa gtaactggtc tgtcgccaga tgttatccag tctatgtcat atttctcttt    4860
ctatggtgat gatgaaatag tgtcaactga catagaattt gatccagcaa aactaacaca    4920
agttctcaga gagtatggac ttaaaccccac ccgccccgac aaaagcgagg gcccaataat    4980
tgtaaggaag aatgtggatg gtttggtctt tttacgtcgc actatctccc gtgacgctgc    5040
gggattccaa ggacgactgg accgagcatc cattgagaga caaatctact ggactagagg    5100
acccaaccat tcagacccctt ttgagaccct ggtgccacac caacaaagga aggtccaact    5160
aatatcatta ttgggcgagg cctcactgca tggtgaaaag ttttacagga agatttcaag    5220
caaagttatc caggaaatta aaacaggggg tcttagatag tatgtgccag gatgcaaagc    5280
catgttccgt tggatgcggt tccatgacct tggtttgtgg acaggagatc gcaatctcct    5340
gcccgaattt gtaaatgatg atggcgtcta aggacgcccc tcaaagcgct gatgcgcaa    5400
gcggcgcagg tcaactggtg ccggaggtta atacagctga cccccttaccc atggaacccg    5460
tggctgggcc aacaacagcc gtagccactg ctgggcaagt taatatgatt gatccctgga    5520
ttgttaataa ttttgtccag tcaccgcaag gtgagtttac aatttcccct aataataccc    5580
ccggtgatat tttgtttgat ctacaattag gtccacattt aaacccttc ttgtcacatt    5640
tgtcccaaat gtataatggc tgggttgaa acatgagagt taggattctc cttgctggga    5700
atgcattctc agccggaaag attatagtct gttgtgtccc ccctggcttc acatcttcct    5760
ctctcaccat agctcaggct acattgtttc cccatgtgat tgctgatgtg agaacccttg    5820
aaccaataga aatgccctc gaggacgtgc gcaatgtcct ctatcacacc aatgataatc    5880
aaccaacaat gcggctggtg tgtatgctgt acacgccgct ccgcactggt gggggtctg    5940
gtaattctga ttcttttgta gttgctggca gggtgctcac ggccctagt agcgacttca    6000
gtttcttgtt ccttgtcccg cctaccatag aacagaagac tcgggctttt actgtgccca    6060
atatcccctt gcaaaccctta tccaattcta ggtttccttc cctcatccag gggatgattc    6120
tgtcccctga cgcatctcaa gtggtccaat tccaaaatgg acgttgtctt atagatggtc    6180
aactcctagg cactacaccc gccacatcag gacagctgtt cagagtgaga ggaaagataa    6240
atcagggagc ccgcacactc aatctcacag aggtggatgg caagccattc atggcatttg    6300
attcccctgc acctgtgggg ttccccgatt ttggaaaatg tgattggcac atgagaatca    6360
gcaaaacccc aaataacaca agctcaggtg acctatgcg cagtgtcgac gtgcaaaccg    6420
atgtgcaggg ttttgtgcca cacctgggaa gcatacagtt tgatgaagtg ttcaaccatc    6480
ccacaggtga ctacattggc accattgaat ggatttccca gccatctcaca cccccctgga    6540
cagatattaa tttatgggag atccccgatt atggatcatc cctctcccaa gcagctaatc    6600
tggcccccc agtattcccc cctgatttg tgaggctct tgtgtacttt gtttctgctt    6660
ttccaggccc caacaacgc tcagccccga atgatgtgcc ttgtctcctc cctcaagagt    6720
acgtaaccca ctttgtcagt gaacaagccc aacgatggg tgacgcagct ttgctgcatt    6780
atgtcgaccc tgataccaac agaaaccttg gggagttcaa gttatacccct ggaggttacc    6840
tcacctgtgt accaaacggg gtgggtgccg ggcctcaaca gcttccccctt aatggtgtct    6900
ttctctttgt ctcttgggtg tctcgttttt atcagctcaa gcctgtggga acagccagta    6960
cggcaagagg taggcttgga gtgcgccgta tataatggcc caagccatta taggagcaat    7020
tgccgcgtca gctgctggct cagcattggg tgcgggcatc caggctggtg ccgaagctgc    7080
gcttcagagt cagagatacc aacaagactt agccctgcaa aggaatacct ttgaacatga    7140
taaagatatg ctttcctacc aggttcaggc aagtaatgcg ctcttagcaa agaatctcaa    7200
tacccgctat tctatgctta ttgcaggagg tctttctaat gctgatgctt ctcgggctgt    7260
tgctggagcc ccagtaacac aattgattga ttggaacggc actcgtgttg ctgccccag    7320
atcagatgca acaactctga ggtcggtgg ttttatggca gtccccatgc ctgttcaacc    7380
caaatctaag gccccgcaat cctctgggtt ctctaatcct gcttatgata tgtccacagt    7440
ttcctctagg acttcttcct gggtgcagtc acagaattcc ctgcgaaatg tgtcaccatt    7500
ccataggcag gccctgcaga ctgtatgggt cactccacct gggtctactt cttcttcttc    7560
tgttctcca acaccttatg gtgtttttaa tacggataggg atgccgctat cgcaaatttt    7620
gcggcgctaa tgttgtaata taatgcagca gtgggcacta tattcaattt ggtttaatta    7680
gtaaataatt tggctattg                                                7699
```

```
SEQ ID NO: 2              moltype = DNA  length = 87
FEATURE                   Location/Qualifiers
source                    1..87
                          mol_type = unassigned DNA
                          organism = unidentified
                          note = Norovirus Hu/GI.2/Leuven/2003/BEL
SEQUENCE: 2
cgttggatgc ggttccatga ccttggtttg tggacaggag atcgcaatct cctgcccgaa    60
tttgtaaatg atgatggcgt ctaagga                                       87

SEQ ID NO: 3              moltype = DNA  length = 7559
FEATURE                   Location/Qualifiers
source                    1..7559
                          mol_type = unassigned DNA
                          organism = unidentified
                          note = Norovirus Hu/Houston/TCH186/2002/US
SEQUENCE: 3
gtgaatgaag atggcgtcta acgacgcttc cgctgccgct gttgctaaca gcaacaacga    60
caccgcaaaa tcttcaagtg acggagtgct ttctagcatg gctgtcactt ttaaacgagc   120
cctcggggcg cggcctaaac agccccccc gagggaaata ccacaaagac ccccacgacc   180
acctactcca gaactggtca aaaagatccc cctcccccg cctaacgag aggatgagat   240
agtggtttct tatagtgtca aagtaggtgt ttccggtttg cctgagcttt ccaccgtcag   300
gcaaccggaa gaagctaata cggccttcag tgtcccccca ctcaatcaga gggagaatag   360
agatgctaag gagccactga ctggaacaat tctggaaatg tgggatggag aaatctacca   420
ttatggcctg tatgtggagc gaggtcttgt actaggtgtg cacaagccac cagctgccat   480
tagcctcgcc aaggtcgaac taacaccact ctccttgttc tggagacctg tgtatactcc   540
tcagtacctc atctctccag acactctcaa gaaattacat ggagaaacgt ttccctacac   600
agcctttgac aacaattgct atgccttttg ttgctgggtc ctggacctaa acgactcgtg   660
gctgagtagg agaatgatcc agagaacaac tggcttcttc agaccctacc aagattgaaa   720
taggaaaccc ctccccacta tggatgattc caaattaaag aaggtagcta acatattcct   780
gtgtgccctg tcttcgctat tcaccaggcc cataaaagac ataataggga agctaaggcc   840
tcttaacatc ctcaacatct tggcttcatg tgattggact ttcgcaggca tagtggagtc   900
cttgatactc ttggcagagc tctttggagt tttctggaca ccccagatg tgtctgcgat   960
gattgccccc ttactcggtg attacgagtt gcaaggacct gaagacctg cagtggagct  1020
cgtccctgta gtgatggggg gaattggtct ggtgctggga ttcaccaaag agaagattgg  1080
aaaaatgttg tcatctgctg catccacctt gagggcttgt aaagatcttg gtgcatatgg  1140
gctagagatc ctaaagttgg tcatgaagtg gttcttcccg aagaaagagg aagcaaatga  1200
actggctatg gtgagatcca tcgaggatgc agtgttggac ctcgaggcaa tcgaaaacaa  1260
ccatatgacc accttgctca aggacaaaga tagtctggca acctacatga gaaccctga  1320
cctcgaggaa gagaaagcca gaaaactctc aaccaagtct gcttcacctg acatcgtggg  1380
cacaatcaac gcccttttgg cgagaatcgc tgctgcacgt tccctggtgc atcgagcgaa  1440
ggaggaactt ccagcagaca caagacctgt agtcttaatg atatcaggca gaccaggaat  1500
agggaagacc caccttgcta gggaagtggc taagagaatc gcagcctctc tcacaggaga  1560
ccagcgtgta ggcctcgtcc cacgcaatgg cgtcgatcac tgggatgcgt acaaggggga  1620
gagggtcgtc ctatgggacg actatggaat gagcaatccc atccgacgg ccctcaggtt  1680
gcaagaactc gctgacactt gcccctcac tctaaactgt gacaggattg agaataaagg  1740
aaaggttttt gacagcgatg tcatcattat cactactaga ctagctaacc cagcaccact  1800
ggactatgtc aactttgaag catgctcgag gcgtatcgat ttcctcgtgt atgcagaagc  1860
ccctgaagtc gaaaaggcga agcgtgactc ccaggccaa cctgacatgt ggaagaacgc  1920
ttttagttct gatttctcac acataaaact gacactggct ccacagggtg ctttgataa  1980
gaacgggaac accccacacg gaagggcgt catgaagact ctcactaccg gctccctta  2040
tgcccgggca tcaggctac tccatgagag gctagatgaa tttgaactac agggcccaac  2100
tctcaccacc ttcaactttg atcgcaacaa agtgcttgcc tttaggcagc ttgctgctga  2160
aaacaaatat gggttgatgg acacaatgaa agttgggagg cagctcaagg atgtcagaac  2220
catgccagaa cttaaacaag cactcaagaa tatctcaatc aagaagtcc agatagtgta  2280
cagtggttgc acctacacac ttgagtctga tggcaagggc aatgtgaaag ttgacagagt  2340
tcagagcgcc tccgtgcaga ccaacaatga gctgactggc gccctgcacc acctaaggtg  2400
cgccagaatc aggtactatg tcaggtgtgt tcaggaggcc ctgtattcca tcatccagat  2460
tgctggggcc gcatttgtca ccacgcgcat cgtcaagcgt atgaacatac aagacctatg  2520
gtccaagcca caagtggaaa acacagagga ggctaccaac aaggacgggt gcccaaaacc  2580
cagagatgat gaggagttcg tcatttcgtc cgacgacatt aaaactgagg gtaagaaagg  2640
gaagaacaag accggccgtg gcaagaaaca cacagccttc tcaagcaaag gtctcagtga  2700
tgaggagtac gatgagtaca agaggattag aagaaagg aatggcaagt actccataga  2760
agagtacctt caggacaggg acaaaatacta tgaggtg ccagtgcca gggcgaccga  2820
ggaagacttc tgtgaagagg aggaggccaa gatccggcaa aggatcttca ggccaacaaa  2880
gaaacaacgc aaggaagaaa gacttctct cggtttggtc acaggttctg aaattaggaa  2940
aagaaaccca gatgatttca gcccaagggg aaactgtgg gctgacgatg acagaagtgt  3000
ggactacaat gagaaactca gttttgaggc cccaccaagc atctggtcga ggatagtcaa  3060
ctttggttca ggttgggct tctgggtctc ccccagtctg ttcataacat caacccacgt  3120
ataccccag ggcgcaaagg aattcttgg agtcccatc aaacaaattc aggtacacaa  3180
gtcaggcgaa ttctgtcgct tgagattccc gaaaccaatc aggactgatg tgacgggcat  3240
gatcttagaa gaaggtgcgc cgaaggcac cgtggtcaca ctactcatca aaggtctac  3300
tggagaactc atgcccctag cagctagaat ggggacccat gcaaccatga aaattcaagg  3360
gcgcactgtt ggaggtcaaa tggcatgct tctgacagga gtcaatgcca aagcatgga  3420
tctaggcacc acaccaggtg attgcggctg tcctactc tacaagagga aatgacta  3480
tgtggtcatt ggagtccaca cggctgccgc tcgtggggga aacactgtca tatgccac  3540
tcagggggagt gaggggagg ctacacttga aggtggtgac agtaagggaa catattgtgg  3600
tgcgccaatc ctaggcccag ggagtgcccc aaaacttagc accaaaacca aattctgag  3660
atcgtccaca gcaccactcc cacctggcac ctatgaacca gcctatctg gtggcaagga  3720
```

```
ccccagagtc aagggtggcc cttcgttgca gcaagtcatg agggatcagc tgaaaccatt   3780
tacagagccc aggggtaagc caccaaagcc aagtgtgtta gaagctgcca agaaaaccat   3840
catcaatgtc cttgaacaaa caattgaccc acctgagaaa tggtcgttcg cacaagcttg   3900
cgcgtccctc gacaagacca cttctagtgg ccatccgcac cacatgcgga aaaacgactg   3960
ctggaacggg gaatccttca caggcaagct ggcagaccag gcttccaagg ccaacctgat   4020
gttcgaagaa gggaagaaca tgaccccagt ctacacaggt gcgcttaagg atgaattagt   4080
caaaactgac aaaatttatg gtaagatcaa gaagaggctt ctctggggtt cggatttagc   4140
gaccatgatc cggtgtgctc gagcattcgg aggcctaatg gatgaactca aagcacactg   4200
tgttacactt cctatcagag ttggtatgaa tatgaatgag gatggcccca tcatcttcga   4260
gaggcattcc aggtacagat accactatga tgctgattac tctcggtggg attcaacaca   4320
acagagagcc gtgttggcag ctgctctaga agtcatggtt aaattctcct cagaaccaca   4380
tttggctcag gtagtcgcag aagaccttct ttctcctagc gtggtggatg tgggtgactt   4440
cacaatatcg atcaacgagg gtcttccctc tggggtgccc tgcacctccc aatggaactc   4500
catcgcccac tggcttctca ctctctgtgc gctctctgaa gttacaaatt tgtccctga    4560
catcatacag gctaattccc acttctcctt ttatggtgat gacgaaattg ttagtacaga   4620
cataaaatta gacccagaga agttgacagc aaaacttaag gaatatggat tgaaaccaac   4680
ccgcccctga aagactgaag gacctcttgt tatctctgaa gacttaaatg gtctgacttt   4740
cctgcggaga actgtgaccc gcgacccagc tggttggttt ggaaaactgg agcagagctc   4800
aatactcagg caaatgtact ggactagagg ccccaaccat gaagacccat ctgaaacaat   4860
gattccacac tcccaaagac ccatacaatt gatgtcccta ctgggagagg ccgcactcca   4920
cggcccaaca ttctacagca aaatcagcaa gttagtcatt gcagagctaa agaaggtgg    4980
tatggatttt tacgtgccca gacaagagcc aatgttcaga ttggatgagt tctcagatct   5040
gagcacgtgg gagggcgatc gcaatctggc tcccagcttt gtgaatgaag atggcgtcga   5100
gtgacgccag cccatctgat gggtccacag ccaacctcgt cccagaggtc aacaatgagg   5160
ttatggcttt ggagcccgtt gttggtgccg caattgcggc acctgtagcg ggccaacaaa   5220
atgtaattga cccctggatt agaaataatt ttgtacaagc ccctggtgga gagttcacag   5280
tatcccctag aaacgctcca ggtgaaatac tatggagcgc gcccttgggc cctgatctga   5340
atccctacct ttctcatttg gccagaatgt acaatggtta tgcaggtggt tttgaagtgc   5400
aggtaattct cgcggggaac gcgttcaccg ccgggaaaat catatttgca gcagtcccac   5460
caaatttccc aactgaaggc ttgagcccca gccaggtcac tatgttcccc catataatag   5520
tagatgttaa gcaactggaa cctgtgttga ttcccttacc tgatgtcagg aataatttct   5580
atcactataa tcagtcaaat gaccccacca ttaaactgat agcaatgctg tacacaccac   5640
ttagggctaa taatgctggg gatgatgtct tcacagtctc ttgccgagtc ctcacgaggc   5700
catccctga ttttgatttt atattttgg tgccacccac agttgagtca agaaccaaac    5760
cattcaccgt cccaattta actgttgagg agatgaccaa ttcaagattc cccattcctt    5820
tggaaaagtt gttcacgggt cccagcgtg cctttgttgt tcaaccacaa aatggcagat    5880
gcacgactga tggcgtgctc ttaggtacta cccaactgtc tcctgttaac atctgcactt   5940
tcagagggga tgtcacccac attgcaggca ctcatgatta caatgaat ttggcttctc     6000
aaaattggaa caattacgac ccaacagaag aaatcccagc ccctctggga actccagatt   6060
tcgtgggaaa gatccaaggc gtgctcactc aaaccacaag gggagatggc tcgacccgtg   6120
gccacaaagc cacagtgagc actgggagtg tccactttac tccaaagctg gcagtgttc    6180
aattcaccac tgacacaaac aatgatcttg aaactggcca aaacacgaaa ttcaccccag   6240
tcggtgtcgt ccaggatggt aatagtgccc accaaaatga ccccaacaa tgggtgtcc    6300
caaattactc aggtagaact ggccataatg tacacctagc ccctgccgta gcccccactt   6360
ttccgggtga gcaacttctc ttcttcaggt ccactatgcc cggatgcagc gggtatccca   6420
acatgaattt ggattgccta ctcccccagg aatgggtgct gcacttctac caagaggcag   6480
ctccagcaca atctgatgtg gctctgctga gatttgtgaa tccagacaca ggtagggtcc   6540
tgtttgagtg caaacttcat aaatcaggct atgtcacagt ggctcacact ggcccgcatg   6600
atttggtcat ccccccaat ggctacttca gatttgattc ctgggttaac caattctaca   6660
cgcttgcccc catgggaaat ggagcggggc gtagacgtgc gttataatgg ctggagcttt   6720
ctttgctgga ttggcatctg atgtccttgg ctctggactt ggttccctaa tcaatgctgg   6780
ggctggggcc atcaaccaaa aagttgaatt tgaaataaac agaaaattgc aacaagcttc   6840
ctttcaattt agcagcaatc tacaacaggc ttccttcaa catgataaag agatgctcca   6900
agcacaaatt gaggccacta aaagttgca acagggtatg atggaagtta aacaggcaat   6960
gctcttagag ggtggattct ctgaaacaga tgcagcccgt ggggcaatca acgcccccat   7020
gacaaaggct ttggattgga gcggaacaag gtactgggct cctgatgcta ggactacaac   7080
atacaatgca ggccgctttt ccaccctca acctttgggg gcactgccag gaagaattaa    7140
tcccagggct cctgccccg ctcagggctc ctccagcaca ccctctagta cttctactgt   7200
tacttctgtg tattcaaatc aaactgttc aacgagactt ggttctacag ctggttctgg   7260
caccagtgtc tcgagtctcc cgtcaactgc aaggactagg agctgggttg aggatcaaaa   7320
caggaatttg tcacctttca tgaggggggc tcacaacata tcgttcgtca ccccaccatc   7380
tagtagatct tctagccaag gcacagtctc aaccgtgcct aaagaaattt tggactcctg   7440
gactggcgct ttcaacacgc gcaggcagcc tctcttcgct cacattcgta gcgaggga     7500
gtcacgggtg taatgtgaaa agacaaaatt gattatcttt cttttcttta gtgtctttt    7559
```
```
SEQ ID NO: 4           moltype = DNA   length = 88
FEATURE                Location/Qualifiers
source                 1..88
                       mol_type = unassigned DNA
                       organism = unidentified
                       note = Norovirus Hu/Houston/TCH186/2002/US
SEQUENCE: 4
tgttcagatg gatgagattc tcagatctga gcacgtggga gggcgatcgc aatctggctc   60
ccagctttgt gaatgaagat ggcgtcga                                      88
```

```
SEQ ID NO: 5             moltype = DNA   length = 20
FEATURE                  Location/Qualifiers
source                   1..20
                         mol_type = other DNA
                         organism = synthetic construct
                         note = Description of Artificial Sequence: Synthetic primer
modified_base            12
                         mod_base = OTHER
                         note = Inosine
SEQUENCE: 5
cgytggatgc gnttycatga                                                       20

SEQ ID NO: 6             moltype = DNA   length = 24
FEATURE                  Location/Qualifiers
source                   1..24
                         mol_type = other DNA
                         organism = synthetic construct
                         note = Description of Artificial Sequence: Synthetic primer
SEQUENCE: 6
tccttagacg ccatcatcat ttac                                                  24

SEQ ID NO: 7             moltype = DNA   length = 29
FEATURE                  Location/Qualifiers
source                   1..29
                         mol_type = other DNA
                         organism = synthetic construct
                         note = Description of Artificial Sequence: Synthetic probe
modified_base            16
                         mod_base = OTHER
                         note = Inosine
SEQUENCE: 7
tggacaggag aycgcnatct cytgcccga                                             29

SEQ ID NO: 8             moltype = DNA   length = 29
FEATURE                  Location/Qualifiers
source                   1..29
                         mol_type = other DNA
                         organism = synthetic construct
                         note = Description of Artificial Sequence: Synthetic probe
SEQUENCE: 8
tggacaggag atcgcaatct actgcctga                                             29

SEQ ID NO: 9             moltype = DNA   length = 25
FEATURE                  Location/Qualifiers
source                   1..25
                         mol_type = other DNA
                         organism = synthetic construct
                         note = Description of Artificial Sequence: Synthetic primer
modified_base            23
                         mod_base = OTHER
                         note = Inosine
SEQUENCE: 9
tgttyaggtg gatgagrttc tcnga                                                 25

SEQ ID NO: 10            moltype = DNA   length = 21
FEATURE                  Location/Qualifiers
source                   1..21
                         mol_type = other DNA
                         organism = synthetic construct
                         note = Description of Artificial Sequence: Synthetic primer
SEQUENCE: 10
tcgacgccat cttcattcac a                                                     21

SEQ ID NO: 11            moltype = DNA   length = 23
FEATURE                  Location/Qualifiers
source                   1..23
                         mol_type = other DNA
                         organism = synthetic construct
                         note = Description of Artificial Sequence: Synthetic probe
SEQUENCE: 11
acgtgggagg gcgatcgcaa tct                                                   23

SEQ ID NO: 12            moltype = DNA   length = 69
FEATURE                  Location/Qualifiers
source                   1..69
                         mol_type = other DNA
                         organism = synthetic construct
                         note = Description of Artificial Sequence: Synthetic
                         oligonucleotide
```

```
SEQUENCE: 12
ctcgtcgaca atggcggaac tggcgacgtg actgtcgccc caagcaactt cgctaacggg    60
gtcgctgaa                                                            69

SEQ ID NO: 13           moltype = DNA  length = 19
FEATURE                 Location/Qualifiers
source                  1..19
                        mol_type = other DNA
                        organism = synthetic construct
                        note = Description of Artificial Sequence: Synthetic primer
SEQUENCE: 13
ctcgtcgaca atggcggaa                                                 19

SEQ ID NO: 14           moltype = DNA  length = 18
FEATURE                 Location/Qualifiers
source                  1..18
                        mol_type = other DNA
                        organism = synthetic construct
                        note = Description of Artificial Sequence: Synthetic primer
SEQUENCE: 14
ttcagcgacc ccgttagc                                                  18

SEQ ID NO: 15           moltype = DNA  length = 23
FEATURE                 Location/Qualifiers
source                  1..23
                        mol_type = other DNA
                        organism = synthetic construct
                        note = Description of Artificial Sequence: Synthetic probe
SEQUENCE: 15
gcttggggcg acagtcacgt cgc                                            23
```